US006637463B1

(12) United States Patent
Lei et al.

(10) Patent No.: US 6,637,463 B1
(45) Date of Patent: Oct. 28, 2003

(54) MULTI-CHANNEL MICROFLUIDIC SYSTEM DESIGN WITH BALANCED FLUID FLOW DISTRIBUTION

(75) Inventors: Ming Lei, Midvale, UT (US); Nils B. Adey, Salt Lake City, UT (US); Michael R. McNeely, Sandy, UT (US)

(73) Assignee: BioMicro Systems, Inc., Salt Lake City, UT (US)

( * ) Notice: Subject to any disclaimer, the term of this patent is extended or adjusted under 35 U.S.C. 154(b) by 0 days.

(21) Appl. No.: 10/142,555

(22) Filed: May 10, 2002

Related U.S. Application Data

(63) Continuation-in-part of application No. 10/060,442, filed on Jan. 30, 2002, which is a continuation-in-part of application No. 09/967,402, filed on Sep. 27, 2001, which is a continuation of application No. 09/417,691, filed on Oct. 13, 1999, now Pat. No. 6,296,020.

(60) Provisional application No. 60/259,209, filed on May 11, 2001, provisional application No. 60/138,092, filed on Jun. 8, 1999, and provisional application No. 60/103,970, filed on Oct. 13, 1998.

(51) Int. Cl.$^7$ ............................................. F15B 21/00

(52) U.S. Cl. ...................... 137/803; 137/806; 137/841; 204/451; 204/601

(58) Field of Search ...................... 137/806, 833, 137/841; 204/451, 601

(56) References Cited

U.S. PATENT DOCUMENTS

| | | | |
|---|---|---|---|
| 3,327,726 A | 6/1967 | Hatch, Jr. | ................... 137/806 |
| 3,417,770 A | 12/1968 | Denison | ..................... 137/806 |
| 3,799,742 A | 3/1974 | Coleman | |
| 3,993,062 A | 11/1976 | Jess | ............................ 128/214 |
| 4,426,451 A | 1/1984 | Columbus | |

(List continued on next page.)

FOREIGN PATENT DOCUMENTS

| | | |
|---|---|---|
| EP | 0933126 A1 | 8/1999 |
| EP | 1016864 A2 | 7/2000 |
| WO | WO 97/02357 | 1/1997 |

(List continued on next page.)

OTHER PUBLICATIONS

Banerjee, "Structured custom design for LOC applications.," ASME Microfluidic for Lab–on–Chip (LOC) Pre-Seminar Workshop, Sep. 9, 2001.

Zeng, Jun et al., "Design Analyses of Capillary Burst Valves in Centrifugal Microfluidics," Technical Proceedings of mTAS (Micro analysis systems) May 2000 conference, Ensched., The Netherlans, p. 493–496.

Duffy, David C., et al., "Microfabricated Centifrugal Microfluidic Systems: Characterization and Multiple Enzymatic Assays," Analytical Chemistry, vol. 71, No. 20., Oct. 15, 1999, 4669–4678.

(List continued on next page.)

Primary Examiner—A. Michael Chambers
(74) Attorney, Agent, or Firm—Madson & Metcalf

(57) ABSTRACT

Methods and apparatus are presented for controlling fluid flow through flow paths with pressure gradient fluid control. Passive fluid flow barriers may be used to act as valves, thereby allowing the flow of fluids through flow paths to be regulated so as to allow fluids to be introduced via a single channel and subsequently split into multiple channels. Flow through the flow paths can be regulated to allow a series of sister wells or chambers to all fill prior to the fluid flowing beyond any one of the sister wells or chambers. Each flow path may have multiple segments, at least one of which is designed to balance the pressure drops of the flow paths to provide uniform flow of fluids through the flow paths. The configurations of the wells may also be modified by adding vents or flow dividers to enhance fluid flushing and gas removal capability.

59 Claims, 6 Drawing Sheets

U.S. PATENT DOCUMENTS

| | | | |
|---|---|---|---|
| 4,618,476 A | | 10/1986 | Columbus .................... 422/100 |
| 4,676,274 A | | 6/1987 | Brown ........................ 137/806 |
| 4,756,884 A | | 7/1988 | Hillman et al. ................ 422/73 |
| 4,868,129 A | | 9/1989 | Gibbons et al. |
| 4,946,795 A | | 8/1990 | Gibbons et al. |
| 4,963,498 A | * | 10/1990 | Hillman et al. ................ 436/69 |
| 5,051,182 A | | 9/1991 | Wang et al. ........... 210/500.27 |
| 5,077,017 A | | 12/1991 | Gorin et al. |
| 5,104,813 A | | 4/1992 | Besemer et al. ............ 436/179 |
| 5,119,116 A | * | 6/1992 | Yu ......................... 346/140 R |
| 5,223,219 A | | 6/1993 | Subramanian et al. ........ 422/55 |
| 5,230,866 A | | 7/1993 | Shartle et al. ............... 422/103 |
| 5,296,375 A | | 3/1994 | Kricka et al. ................ 435/291 |
| 5,304,487 A | * | 4/1994 | Wilding et al. ................ 435/29 |
| 5,378,504 A | | 1/1995 | Bayard et al. ................ 426/377 |
| 5,427,946 A | | 6/1995 | Kricka et al. ................ 435/291 |
| 5,486,335 A | | 1/1996 | Wilding et al. ................ 422/55 |
| 5,498,392 A | | 3/1996 | Wilding et al. ............ 422/68.1 |
| 5,587,128 A | * | 12/1996 | Wilding et al. ................ 422/50 |
| 5,635,358 A | | 6/1997 | Wilding et al. .............. 435/7.2 |
| 5,637,469 A | | 6/1997 | Wilding et al. ............ 435/7.21 |
| 5,726,026 A | | 3/1998 | Wilding et al. ............ 435/7.21 |
| 5,726,404 A | | 3/1998 | Brody ....................... 200/81 R |
| 5,730,187 A | | 3/1998 | Howitz et al. .............. 137/833 |
| 5,744,366 A | | 4/1998 | Kricka et al. .................. 436/63 |
| 5,846,396 A | | 12/1998 | Zanzucchi et al. .......... 204/601 |
| 5,856,174 A | | 1/1999 | Lipshutz et al. ......... 435/286.5 |
| 5,866,345 A | * | 2/1999 | Wilding et al. ............ 435/7.21 |
| 5,869,004 A | | 2/1999 | Parce et al. .................. 422/100 |
| 5,900,130 A | | 5/1999 | Benvegnu et al. .......... 204/453 |
| 5,910,287 A | | 6/1999 | Cassin et al. |
| 5,922,591 A | | 7/1999 | Anderson et al. ........... 435/287 |
| 5,922,604 A | | 7/1999 | Stapleton et al. ............. 436/46 |
| 5,928,880 A | | 7/1999 | Wilding et al. ............ 435/7.21 |
| 5,955,029 A | | 9/1999 | Wilding et al. ............ 422/68.1 |
| 5,958,344 A | | 9/1999 | Levine et al. ................ 422/103 |
| 5,976,336 A | | 11/1999 | Dubrow et al. ............. 204/453 |
| 5,980,719 A | | 11/1999 | Cherukuri et al. .......... 204/600 |
| 5,992,820 A | | 11/1999 | Fare et al. ............. 251/129.01 |
| 6,004,515 A | | 12/1999 | Parce et al. .................. 422/100 |
| 6,043,080 A | | 3/2000 | Lipshutz et al. ......... 435/287.2 |
| 6,046,056 A | | 4/2000 | Parce et al. .................. 436/514 |
| 6,048,498 A | | 4/2000 | Kennedy ..................... 422/99 |
| 6,068,752 A | | 5/2000 | Dubrow et al. ............. 204/604 |
| 6,086,740 A | | 7/2000 | Kennedy .................... 204/601 |
| 6,086,825 A | | 7/2000 | Sundberg et al. ........... 422/100 |
| 6,193,471 B1 | | 2/2001 | Paul ............................ 417/53 |
| 6,207,031 B1 | | 3/2001 | Adourian et al. ............ 204/451 |
| 6,296,020 B1 | * | 10/2001 | McNeely et al. ........... 137/806 |
| 6,391,622 B1 | | 5/2002 | Knapp et al. ............ 435/285.2 |

FOREIGN PATENT DOCUMENTS

| | | |
|---|---|---|
| WO | WO 98/29736 | 7/1998 |
| WO | WO 98/56505 | 12/1998 |
| WO | WO 99/56954 | 11/1999 |
| WO | WO 99/64836 | 12/1999 |
| WO | WO 00/21659 | 4/2000 |
| WO | WO 01/41931 | 6/2001 |
| WO | WO 01/88525 | 11/2001 |
| WO | WO 01/90614 | 11/2001 |
| WO | WO 02/22464 | 3/2002 |

OTHER PUBLICATIONS

Man, P.F., et al., "Microfabricated Capillary–Driven Stop Valve and Sample Injector." University of Michigan.

Anderson, Rolle C. et al., "Advances in Integrated Genetic Analysis," Affymetrix, Inc.

"Recent Patent in Microfabrication and Microfluidics", Nature Biotechnology, vol. 17, Jun. 1999, p. 606.

Anderson, R. C. et al., "Microfluidic Biochemical Analysis System," Int. Cong. On Solid–State Sens. and Act Transducers, 1997, Chicago, Jun. 16–19, 1997, 477–480.

Brahmasandra, S.N. et al., "A Microfabricated Fluidic Reaction and Separation System for Integrated DNA Analysis," Micro Total Analysis Systems, 1998, D.J. Harrison and A. Van Den Berg. Eds Kluwer Acad Publ. Dordrecht (1998) Proceedings of the $\mu$TAS 1998 Workshop, Banff, Canada, Oct. 13–16, 1998, 307–310 and cover page.

Hosokawa, K. et al., "Hydrophobic Microcapillary Vent for Pneumatic Manipulation of Liquid in $\mu$TAS," *Micro Total Analysis Systems '98*, D.J. Harrison and A. Van den Berg. eds. Kluwer Acad. Publ., Dordrecht (1998); Proceedings of the $\mu$TAS '98 Workshop, Banff,Canada, Oct. 13–16, 1998; pp. 307–310 and cover page.

Lee, L.P. et al., "Key Elements of Transparent Teflon Microfluidic System," Micro Total Analysis Systems 1998, D.J. Harrison and A. Van den Berg, eds. Kluwer Acad. Publ. Dordrecht (1998); Proceedings of the $\mu$TAS 1998 Workshop, Banff,Canada, Oct. 13–16, 1998, 245–48, cover page.

* cited by examiner

US 6,637,463 B1

MULTI-CHANNEL MICROFLUIDIC SYSTEM DESIGN WITH BALANCED FLUID FLOW DISTRIBUTION

RELATED APPLICATIONS

This application claims the benefit of U.S. Provisional Application No. 60/290,209, filed May 11, 2001, and is a continuation-in-part of U.S. patent application Ser. No. 10/060,442, filed Jan. 30, 2002, which is a continuation-in-part of U.S. patent application Ser. No. 09/967,402, filed Sep. 27, 2001, which is a continuation of U.S. application Ser. No. 09/417,691, filed Oct. 13, 1999, now U.S. Pat. No. 6,296,020, which claims the benefit of U.S. Provisional Application No. 60/103,970, filed on Oct. 13, 1998, and U.S. Provisional Application No. 60/138,092, filed on Jun. 8, 1999. All of the above applications are incorporated herein by reference.

BACKGROUND OF THE INVENTION

1. Field of the Invention

The present invention relates to methods and apparatus for controlling fluid flow through flow paths. More specifically, the present invention relates to microfluidic methods and circuit devices in which flow path configurations are designed to control pressure drops on selected flow path segments to balance fluid flow among multiple flow paths, leading to efficient operation of the wetted microfluidic circuit.

2. Description of Related Art

Controlling the movement of fluids through channels on a micro-scale has important applications in a number of technologies. For example, in the field of molecular biology and diagnostic testing and detection, polymerase chain reactions (PCR) have been performed in a chip containing microfabricated flow channels (U.S. Pat. Nos. 5,498,392, 5,587,128, and 5,726,026). In the electronics field, thermal ink jet printers use print heads with flow paths through which ink must flow in a well-controlled manner (U.S. Pat. No. 5,119,116). Proper control of fluids through flow paths has been a challenge, because microdimensions impart characteristics and behaviors that are not found in larger scale systems, which are due primarily to the greater influence of surface effects.

The term "surface effects" is used to describe specific characteristics of a surface on a micro-scale. Materials often have unbound electrons, exposed polar molecules, or other molecular level features that generate a surface charge or reactivity characteristic. Due to scaling, these surface effects or surface forces are substantially more pronounced in microstructures than they are in traditionally sized devices. This is particularly true in micro-scale fluid handling systems where the dynamics of fluid movement are governed by external pressures and by attractions and repulsions between liquids and the materials of the microfluidic systems through which they flow.

It is frequently the case that micro-scale fluid handling systems are designed to perform multiple fluid handling steps in parallel, and it is often considered desirable to process fluids in multiple parallel flow paths simultaneously. However, such systems frequently suffer from uneven and irregular fluid flow. Many such problems are due to surface effects such as those mentioned above. Some micro-scale fluid systems fill unevenly. In others, channels fill at different rates. Additionally, some fluid circuits that split samples into multiple reaction chambers may do so unevenly. Those combining samples from multiple reaction chambers may do so incompletely or unevenly.

Such problems may result in incomplete assays or assays conducted with insufficient amounts of reagent or sample. Some of these problems may result in differences in the reaction times for the different assays, thus changing the results. These and other problems may affect the accuracy of assays and the usability of the micro-scale fluid handling systems themselves. Furthermore, uneven filling tends to result in the waste of valuable reagent or sample material, because larger volumes of fluid may be required to insure that all portions of the system are filled completely.

Yet further, many known chip designs have several wells. In order to provide the most compact arrangement of wells and flow paths, the flow paths must often be asymmetrical in design. The flow paths may thus provide different resistances to the flow of fluids filling the wells or draining from the wells. The presence of differential resistance to flow contributes to the unevenness with which the wells are filled and emptied, and therefore further reduces the accuracy of the assay.

Still further, many microfluidic circuits have well designs in which, due to the configuration of the well, fluids tend to stagnate within the well rather than exiting upon entry of a different fluid. Hence, samples or reagents within the well may not be washed or flushed properly at lower pressures. Additionally, gas bubbles, which may skew the results of the assay, may not be effectively removed from the wells. The use of higher volumes may improve washing but results in waste or inefficient use of limited sample and increased reagent costs.

Accordingly, a need becomes apparent for microfluidic circuits in which fluid flow may be regulated. Fluid flow should preferably be well-controlled during both the initial filling of the unwetted circuit and during subsequent introduction of additional reagents or wash solutions to the wetted circuit, so that gas removal and liquid exchange or flushing can be effectively carried out. Preferably, such regulation can be performed with flow paths and wells that are laid out in a compact, and possibly asymmetrical, fashion. Furthermore, a need exists for fluid circuits, and associated well structures, that can be reliably flushed to remove a liquid or gas at a low pressure and with a low volume of fluid. Such fluid circuits and methods for their use are disclosed herein.

SUMMARY OF THE INVENTION

The apparatus of the present invention has been developed in response to the present state of the art, and in particular, in response to the problems and needs in the art that have not yet been fully solved by currently available micro-scale fluid handling systems, also called microfluidics systems.

Thus, the present invention discloses a system and method for controlling the flow of fluids through microchannels in multiple parallel flow paths in such a manner that fluid can be evenly distributed among several parallel channels for multiprocessing. The parallel flow paths are configured to have uniform resistances to fluid flow so that fluid is induced to flow through all of the flow paths at substantially the same flow rate. One or more segments of each flow path may be specially configured to provide a desired relative pressure drop to, so that the pressure gradients can be equalized even though the flow paths may not be symmetrical or coextensive to each other.

According to certain embodiments, the flow of the fluid front through the flow paths is initially controlled by structures that act as passive fluid flow barriers, which in the present invention are abrupt changes in the geometry or surface properties of certain portions of the flow paths. These passive fluid flow barriers act to stop fluid flow by creating a passive pressure barrier that may be overcome by sufficient pressure, or by wetting both sides of the barrier.

Unlike flow barriers that require moving parts, the passive fluid flow barriers or abrupt flow path widenings can be static and their operation does not depend upon the use of moving parts. They are thus cheaper and simpler to construct than the various types of microelectromechanical active valves, and they do not require external controls.

According to certain embodiments, a microfluidic circuit within the scope of the invention may have a plurality of flow paths branching from a common inlet. Each flow path may have a filling portion that supplies fluid to an associated well or structure, and a draining portion that receives fluid from the well or structure for collection, further processing, or disposal. Throughout the specification, any such structures, which serve as sites at which chemical reactions and/or read-outs take place, will simply be referred to as wells. However, it should be understood that a well is just an example of a fluid handling structure that may be included in the flow path, and the flow path could include other fluid handling structures, e.g., a combination of several wells in series or parallel, channels or chambers of various dimensions, or chambers containing a matrix material, such as a filter, separation, or binding medium, including fibers, resins, beads or other materials. Any such structures may be used in the practice of the present invention, providing it is possible to identify the contribution of the fluid processing structure to the resistance to fluid flow and pressure drop over that portion of the flow path.

The common inlet may feed a main distribution channel. The wells may be disposed on one or both sides of a main distribution channel that incorporates a portion of at least some of the flow paths. The wells may be disposed in a row. Entrance channels may branch off the main distribution channel at intervals to deliver fluid to wells. The filling portion of each flow path is then made up of the entrance channel and the portion of the main distribution channel leading from the common inlet to the entrance channel. The wells or structures may be arranged in a compact manner to increase the number of wells or structures on a single chip.

Each of the wells or structures may be separated from the draining portion of the associated flow path by a passive fluid flow barrier. More specifically, a plurality of exit channels may intersect each of the wells. The exit channels may be somewhat narrow so that the juncture of each exit channel with a well is a narrowing with the proper geometry to form a passive pressure barrier. The intersection of multiple exit channels with each well may serve to draw fluid from multiple regions of the well simultaneously, thereby avoiding the formation of recirculating currents or fluid stagnation that may otherwise tend to inefficient washing of fluid, and trapping of air bubbles within the wells.

The exit channels from each well may merge with an extension channel that conveys the fluid to a waste collection channel, and from there to a single system outlet, all of which together make up the draining portion of the flow path. The extension channels on different flow paths may differ from each other so that they do not provide the same pressure gradient or pressure drop. More precisely, the pressure drop of each extension channel may be selected to compensate for the difference in pressure drop between the associated flow path and the remaining flow paths. The extension channels may thus have different lengths, cross sectional areas, surface roughness characteristics, or the like. Hence, the extension channels may be structured in such a manner that all of the flow paths have substantially the flow rate when subjected to the same pressure differential.

Extension channels may intersect the waste channel at different points, so that the length of the waste collection channel included between the extension channel and the common system outlet may differ for the different flow paths. According to one embodiment, the waste collection channel is configured in such a manner that the extension channels have different lengths to provide relative pressure drop compensation. The extension channels may be straight to intersect the waste collection channel at different distances. According to an alternative embodiment, the waste collection channel may be straight, and may run parallel to the distribution of the wells. The extension channels may still be different lengths; each of the longer extension channels may have a serpentine configuration. Varying numbers of bends may be used to vary the lengths of the extension channels.

According to another alternative embodiment, the waste collection channel may again be straight and parallel to the distribution of the wells. The extension channels may all be equal in length, but may have different cross sectional areas. Since the pressure drop across an extension channel is generally inversely proportional to the cross sectional area of the extension channel for a given flow rate, variation of the cross sectional areas may be used to equalize the pressure drops of the flow paths.

In operation, fluid flows from the common inlet, through the filling portion of each flow path and into the associated well, until it is stopped by a passive fluid flow barrier when the well has filled; this occurs until all wells have been filled. When it is desired to flush the fluid from the wells, a second fluid may be injected through the inlet at a pressure high enough to overcome the passive fluid flow barriers. The second fluid then pushes the first fluid out through the exit channels relatively evenly, as a result of the fact that all of the flow paths have substantially the same resistance to fluid flow. Furthermore, the use of multiple exit channels at the outlet of each well contributes to even and efficient washing of the first fluid by the second fluid. Air bubbles may also be flushed out through the exit channels, by virtue of the manner in which the exit channels are positioned.

According to alternative embodiments, the well structures may be further modified to enhance the liquid flushing and/or gas removal characteristics of the microfluidic circuit. For example, air vents may also intersect the well, in addition to the exit channels. The air vents may have a small cross-sectional area by comparison with the exit channels, so that they allow gas, such as air, to pass but create a sufficient pressure barrier to prevent liquid from flowing through the vent. Several such air vents may be distributed about the well to provide relatively complete gas removal.

According to another alternative well structure, flow dividers may be provided within the well. Each flow divider may simply be a wall or surface structure that divides a stream of incoming fluid into two streams. Multiple dividers may be used to provide three or more streams, each of which is directed into a different portion of the well. Hence, stagnant fluid that would otherwise tend to remain in the well may be avoided, and gas or liquid may be more completely flushed from the fluid circuit by the entrance of a second fluid.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
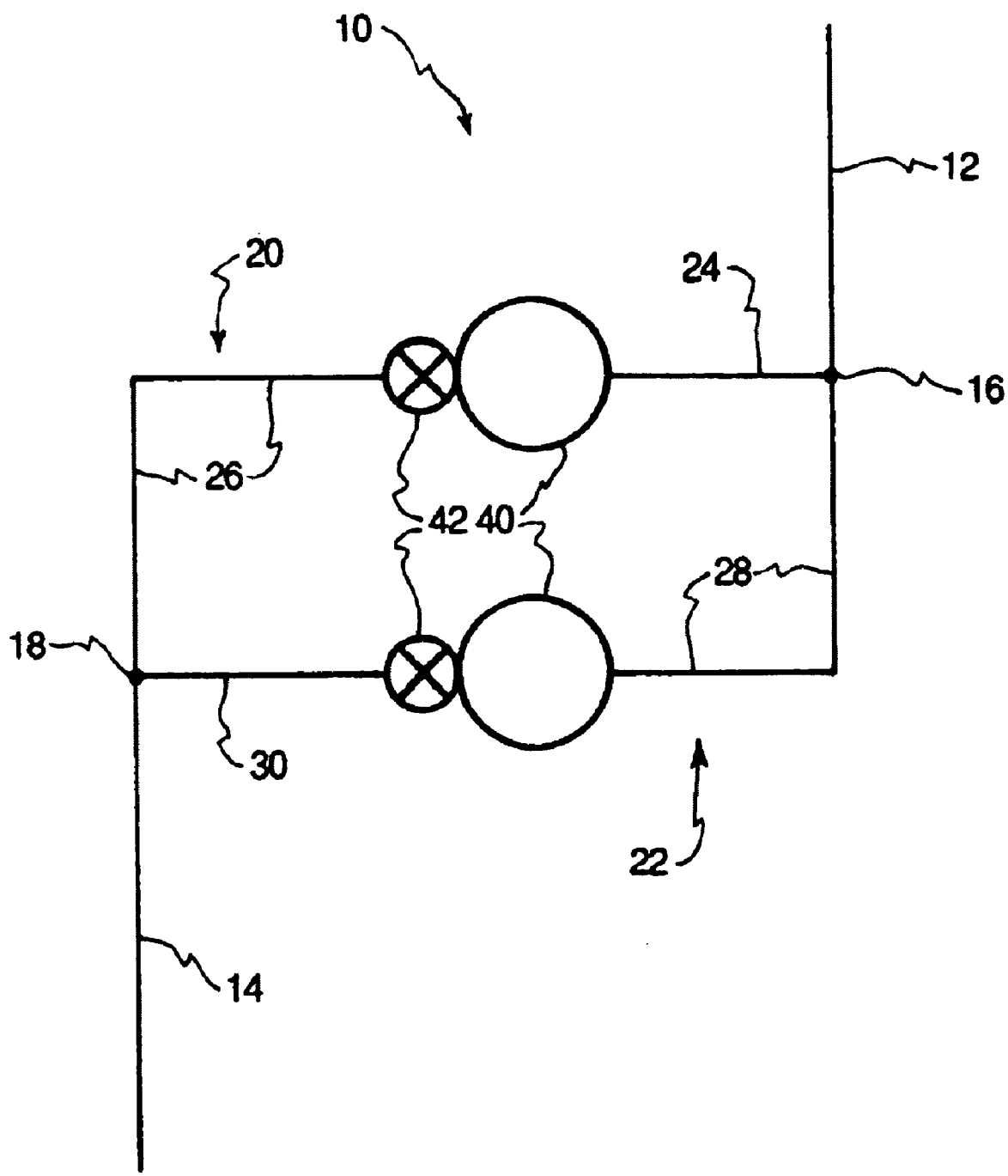
FIG. 1 is a schematic view of an exemplary microfluidic circuit within the scope of the invention.

The presently preferred embodiments of the present invention will be best understood by reference to the drawings, wherein like parts are designated by like numerals throughout. It will be readily understood that the components of the present invention, as generally described and illustrated in the figures herein, can be arranged and designed in a wide variety of different configurations. Thus, the following more detailed description of the embodiments of the apparatus, system, and method of the present invention, as represented in FIGS. 1 through 6, is not intended to limit the scope of the invention, as claimed, but is merely representative of presently preferred embodiments of the invention.

This invention deals with control of fluids within microfluidic circuits. More specifically, the invention utilizes pressure gradient, or pressure drop, balancing among multiple fluid flow paths to equalize the flow rate of fluid through the flow paths. In general, fluid will flow through a flow path if a pressure differential exists between the inlet and outlet of the flow path. Multiple flow paths connected to a common inlet and a common outlet will have identical pressure differentials, but may have different flow rates if flow path configurations differ. In other words, the fluid flow between the common inlet and common outlet will be distributed non-uniformly among the different flow paths. In order to balance flows across all flow paths, a flow paths must be configured to provide uniform resistances to fluid flow. In the present invention, fluid circuits are constructed in which the physical configurations of selected portions of flow paths are modified to compensate for differences in resistance to flow in other portions of the flow paths, which cause non-uniform flow among flow paths. Determination of suitable flow path configuration is facilitated by assuming uniform flow along all flow paths, and identifying the required pressure drop on each flow path segment. Appropriately configured fluid circuits deliver substantially synchronous flow on all flow paths under wetted fluid circuit conditions.

In certain fluid circuits according to the present invention, passive fluid control may also is be utilized, to produce uniform filling upon initial introduction of fluid to the unwetted fluid circuit. This passive control may be generated by using natural forces that exist on a microscale. Specifically, capillarity, which is caused by the attraction or repulsion of a fluid toward certain materials, allows passive control of fluid flow in the fluid circuits of the invention. Herein, the terms passive fluid flow barrier, passive fluid valve, abrupt flow path widening, stopping means, are used to denote structures which stop fluid flow through a flow path by generating a passive pressure barrier.

Passive fluid flow barriers may be produced in a variety of ways, including channel surface modifications, abrupt channel narrowings (in hydrophobic materials if a polar fluid is used, or in hydrophilic materials if a non-polar fluid is used), or channel widenings (in both hydrophilic and hydrophobic materials). Channel narrowings may include narrowings in which only one channel dimension is narrowed. Commonly owned U.S. Pat. No. 6,296,020, incorporated herein by reference, discusses the mathematical and physical properties useful for determining the passive fluid flow barriers generated by modifying parameters of channel radius, contact angle, and surface tension, as well as various microfluidic circuit structures based thereon.

Passive fluid flow barriers may be used to stop fluid flow along one path in a circuit until enough pressure is applied to the fluid to overcome the passive fluid flow barrier and allow fluid to flow past the passive fluid flow barrier, or until the passive fluid flow barrier itself is removed or made insignificant. The pressure barrier that is generated by the passive fluid flow barrier can be utilized to direct fluid through the circuit in some creative manner, or to hold fluid at a specific location. As briefly noted above, the capillary properties of materials used in microfluidic circuits give rise to the passive fluid flow barriers. Fluid flow barriers may be created by changing the cross sectional area of the channel or flow path, by changing the contact angle of the material forming the flow path, or by changing the surface tension of the fluid flowing at the fluid flow barrier. Of course, other fluid flow regulation mechanisms known in the art may be used in place of the passive fluid flow barriers.

Referring to FIG. 1, a schematic view illustrates the operation of an exemplary, simplified microfluidic circuit 10 that utilizes the principles of the invention. The microfluidic circuit 10 (also referred to as circuit 10), may have a single inlet channel 12, through which fluids are introduced into the circuit 10. Inlet channel 12 may be connected to a fill port or fluid inlet on the exterior of the device in which microfluidic circuit 10 is formed, to receive fluid from an outside source, or it may receive fluid from the outlet of an upstream microfluidic circuit. Moreover, it is possible that multiple fluid sources (e.g. multiple separate injection ports for sample, reagents, and wash fluids) may be connected to a single inlet. It should be noted that while sample and reagent fluids will generally be liquids, in some cases air or other gasses or gas mixtures may be injected into inlets in order to drive other (downstream) fluids through the microfluidic circuit. Therefore, the term fluid may refer to either liquids or gases in the practice of the present invention. The circuit 10 may also have an outlet channel 14 through which fluids exit the circuit 10 for further processing, collection, or disposal. Outlet channel 14 may lead to a port communicating with the exterior of the device in which microfluidic circuit 10 is formed, or to a waste reservoir on the device. Outlet channel 14 may also connect to various types of downstream microfluidic circuitry.

The inlet channel 12 may have a branching point 16, at which the fluid branches into multiple passageways, or "flow paths." The flow paths may converge at a converging point 18 of the outlet channel 14 to convey the fluid to the outlet channel 14. As shown, only two flow paths, i.e., a first flow path 20 and a second flow path 22, are illustrated. Subsequent embodiments will show the use of more than two flow paths; any plural number of flow paths is envisioned within the scope of the invention.

For purposes of analysis, the first flow path 20 may be divided into a first segment 24 and a second segment 26. Similarly, the second flow path 22 has a first segment 28 and a second segment 30. The inlet channel 12, in combination with first segments 24, 28 form filling portions that supply fluid to wells 40, each of which is coupled to one of the flow paths 20, 22. The second segments 26, 30, in combination with outlet channel 14, form a draining portion that receive fluid from the wells 40 to convey the fluid to the outlet channel 14.

Each of the wells 40 may simply be a cavity sized to permit the occurrence of chemical or biochemical reaction or other process, the result of which may be detected or measured in some way to determined the outcome of the reaction. The wells 40 may, for example, be seeded with chemical reagents or biological material prior to injection of the fluid; after the fluid has reached the wells 40, the fluid may react with the reagents or material within the wells 40. The fluid may then be flushed from the wells 40, for example, via injection of a second fluid. Hence, it may be desirable for the fluid to reach the wells 40 substantially simultaneously, and to be flushed from the wells 40 substantially simultaneously so that the reactions within the wells 40 have substantially equal time in which to occur. In the design of a fluid circuit according to the present invention, well size sufficient to accommodate the desired reaction is normally selected first, and the sizes of additional components of the circuit are selected in relation to the size of the wells. In place of wells, various other fluid handling structures could be used, such as a combination of several wells in series or parallel, channels or chambers of various dimensions, or chambers containing various matrix materials, as discussed previously.

The flow paths 20, 22 may be structured to provide such generally simultaneous filling and removal of fluid from the wells 40. For example, each of the flow paths 20, 22 may have a valve 42 disposed directly downstream of the wells 40. The valves 42 may operate as check valves that block the flow of fluid into the second segments 26, 30 of the flow paths 20, 22 until the fluid pressure has exceeded an established threshold. The valves 42 may be mechanically, pneumatically, hydraulically, thermally, or electrically operated, or may operate based on passive pressure principles to form passive fluid flow barriers; as described in detail in the related applications.

In any case, the valves 42 keep the fluid within the wells 40 until the reaction is complete. The second fluid may then be injected into the inlet channel 12. If the valves 42 operate based on passive pressure, the second fluid may be injected at higher pressure to induce the first fluid to flow past the valves 42, into the second segments 26, 30. Otherwise, the valves 42 may be actuated into the open position prior to injection of the second fluid, and the second fluid need not be injected at a pressure higher than the initial injection of the first fluid.

If passive fluid flow barriers are used to form the valves 42, the operation of the valves 42 is substantially neutralized once the valves 42 become wetted. Each flow path 20, 22 has a nominal "head loss," or pressure drop estimated for the same expected flow rate. The nominal pressure drop ($\Delta P$) is a measure of energy loss due to friction as the fluid flows against the walls of the flow path 20, 22. Thus, if one of the flow paths 20, 22 has a lower resistance to flow than the other, a greater portion of fluid will flow through the flow path 20, 22 with the lower resistance to flow. The higher the nominal pressure drop, the higher the friction resistance of the flow path to the fluid flow. For a fixed injection pressure, the distribution of flow rates in multiple parallel flow paths is generally inversely proportional the pressure drops of the flow paths.

If fluid flows through the flow paths 20, 22 at different rates, one of the wells 40 will be flushed before the other. Hence, the reaction times of the wells 40 will not be equal, and the results of the testing will be less accurate than if the wells 40 were simultaneously flushed. Additionally, the flushing operation must generally continue until all of the wells 40 have been fully flushed; a greater volume of fluid will generally be required if flushing is completed at different times for each of the wells 40.

In order to obtain the desired balance of flow between flow paths 20 and 22, flow paths 20 and 22 must be configured to provide resistances to flow that will give the desired flow rates at the pressure drop that will be applied between the inlet 11 and outlet 13. Since the flow paths 20, 22 branch from a common inlet channel 12 and converge to a common outlet channel 14, it may be assumed that the pressure drops across the flow paths 20, 22 are equal. It is contemplated that the method of microfluidic circuit design described herein, in which channel configurations that provide uniform flow distributions are selected on the basis of balancing pressure drops, can be used for circuits in which the flow paths do not share both a common branching point and common merge point, and thus have equal pressure drops. Specifically, the pressure drops on the two paths need not be identical, so long as they are known, in relative if not absolute terms. If pressure drops on two different flow paths will be different, but in a known fixed ratio in relation to each other, equal fluid flow rates will be obtained in the two flow paths if the resistances of the two flow paths to fluid flow are selected to have the same known ratio as the pressure drop ratio. Such configurations are included within the scope of the invention; however, for simplicity, the remainder of this description will address a microfluidic circuit that does not contain additional separate, non-balanced elements.

Returning to the flow paths 20, 22 of FIG. 1, each of the segments 24, 26, 28, 30 will have a pressure drop. The pressure drop of the first flow path 20 is equal to the pressure drop of the first segment 24 plus the pressure drop of the second segment 26. Similarly, the pressure drop of the second flow path 22 is equal to the pressure drop of the first segment 28 plus the pressure drop of the second segment 30.

The wells 40 are considered as separate elements for purposes of this analysis; their pressure drops would, in any case, be the same since the wells 40 have the same configuration. The pressure drops of the valves 42 are also the same, and are included within the pressure drops of the second segments 26, 30. Hence, balancing the pressure drops of the flow paths 20, 22 involves equating the pressure drop of the first and second segments 24, 26 of the first flow path 20 with that of the first and second segments 28, 30 of the second flow path 22.

As stated above, the pressure drops over flow paths 20 and 22 will be equal. In order to determine channel configurations that will give the desired equal flow through the two flow paths, the flows through flow paths 20 and 22 will be set to be equal. Certain portions of flow paths 20 and 22 will be configured identically, and thus will have equal resistances to flow, and equal pressure drops at the assumed equal flow rate. Other portions of the flow paths are constrained to different, but known, configurations (depending on their intended uses, for example) that lead to different, known pressure drops. The configurations of other portions of the flow paths may by adjusted as desired. The pressure drops that required on these portion in order to give equal pressure drops over flow paths 20 and 22 as a whole are determined, and then the configurations of the channels are selected to give the necessary pressure drops at the specified flow rate.

The flow resistance (and hence, for a specified flow rate, the pressure drop) of a segment or channel may be modified in a number of ways. For example, flow resistance is generally inversely proportional to the flow area of the channel, and proportional to the length of the channel. The shape of the cross section of the channel also affects the flow resistance of the channel, as some shapes will expose the fluid to a larger wall surface, thereby providing additional friction. The surface characteristics of the channel, such as roughness, may also affect the flow resistance of the channel. For a microfluidic circuit, the easiest parameters to modify may be the length, width, and/or depth of the flow path. Variations in cross sectional shape and surface roughness may be somewhat more difficult, but are also included within the scope of the invention.

The length, width, and/or depth of the segments 24, 26, 28, 30 may be changed in relation to each other to balance the pressure drops of the first and second flow paths 20, 22 under wetted fluid circuit conditions. Through the use of consistent valving and pressure drop balancing, substantially simultaneous filling and flushing of the wells 40 may be carried out to provide reliable and accurate fluid processing. Application of these principles in a functional microfluidic circuit will be more specifically described, with reference to FIG. 2.

Figure 2:
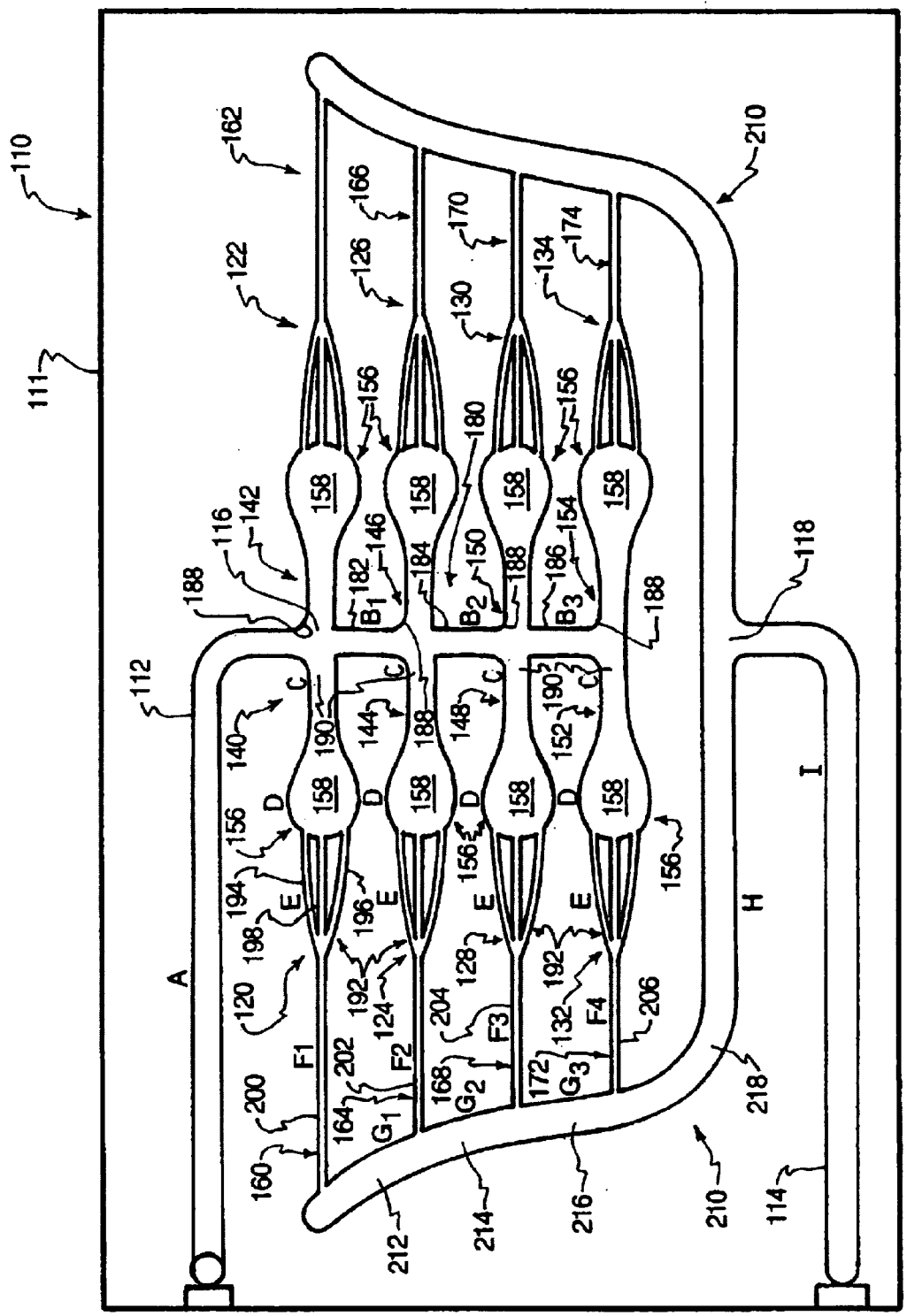
FIG. 2 is a plan view of another embodiment of a microfluidic circuit within the scope of the invention.

Referring to FIG. 2, a plan view illustrates one embodiment of a functional microfluidic circuit 110, or circuit 10. The circuit 110 may be formed in a block, also referred to as a "chip," designated 111. The area of chip 111 in which circuit 110 is formed may range from about ten mm to about 200 mm in width. Furthermore, the area of chip 111 containing circuit 110 may range from about twenty-five mm to about 100 mm in width. Yet further, the area of chip 111 containing circuit 10 may be about fifty mm in width.

Although FIG. 2 is not necessarily actual size, the features of chip 111, as depicted in FIG. 2, may be substantially to scale with respect to each other and to the chip 111. The various channels of the circuit 10 may be formed by molding, micro-machining, lithography, rapid prototyping, laser ablation, and/or other known methods of producing small scale features. The circuit 110 may be covered by a lid to prevent fluid leakage from the circuit 110. Channels may vary in size from a few microns up to a millimeter or two for the larger channels.

The circuit 110 may have an inlet channel 112 that intersects the edge of the chip 111, so that fluid can be injected into the inlet channel 112. An outlet channel 114 may similarly intersect the edge of the chip 111 for fluid removal. In the alternative, the outlet channel 114 may be coupled to some type of fluid collection reservoir stored on the chip 111. The inlet channel 112 may have a branching point 116 from which a plurality of flow paths diverge. Similarly, the outlet channel 114 may have a converging point 118 to which the flow paths converge.

The circuit 110 may have a first flow path 120 and a second flow path 122 symmetrically disposed opposite the first flow path 120. Furthermore, the circuit 110 may have third and fourth flow paths 124, 126, fifth and sixth flow paths 128, 130, and seventh and eighth flow paths 132, 134 displaced from the first and second flow paths 120, 122 to form a double row. The first, third, fifth, and seventh, i.e., odd-numbered flow paths 120, 124, 128, 132 are on the left and the second, fourth, sixth, and eighth, i.e., even-numbered channels 122, 126, 130, 134 are on the right.

The flow paths 120, 122, 124, 126, 128, 130, 132, 134 may have filling portions 140, 142, 144, 146, 148, 150, 152, 154, respectively. Each of the filling portions 140, 142, 144, 146, 148, 150, 152, 154 is disposed upstream of a well structure 156, each of which includes a well 158. Each filling portion 140, 142, 144, 146, 148, 150 152, 154 communicates with one of the wells 158 to deliver fluid to the well 158. Each of the wells 158 may have a rounded configuration with a size suitable for testing. In the alternative to the wells 158, a different type of structure, such as a flat sided even elongated cavity (not shown), may be used. Moreover, various other fluid handling structures may be used in place of wells, as discussed previously.

The flow paths 120, 122, 124, 126, 128, 130, 132, 134 may also have draining portions 160, 162, 164, 166, 168, 170, 172, 174, respectively. Each of the draining portions 160, 162, 164, 166, 168, 170, 172, 174 is disposed downstream of one of the well structures 156. Each well 158 communicates with one of the draining portions 160, 162, 164, 166, 168, 170, 172, 174 to receive fluid for delivery to the outlet channel 114.

Each of flow paths 120, 122, 124, 126, 128, 130, 132, 134, extends from the inlet of the chip to the outlet, and all flow paths overlap with each other at inlet channel 112 and outlet channel 114. Flow paths 120, 122, 124, 126, 128, 130, 132, 134 overlap with each other to varying extents between branching point 116 and converging point 118. More specifically, the first and second flow paths 120, 122 branch from the branching point 116, from which main distribution channel 180 also extends to convey fluid to the remaining flow paths 124, 126, 128, 130, 132, 134. Portions of main distribution channel 180 also may be considered parts of the remaining flow paths 124, 126, 128, 130, 132, 134, as the flow paths 120, 122, 124, 126, 128, 130, 132 134 encompass all flow path elements between the branching point 116 and the converging point 118.

A first segment 182 of the main distribution channel 180 extends between the first and second flow paths 120, 122 and the third and fourth flow paths 124, 126. A second segment 184 extends between the third and fourth flow paths 124, 126 and the fifth and sixth flow paths 128, 130. A third segment 186 extends between the fifth and sixth flow paths 128, 130 and the seventh and eighth flow paths 132, 134.

The main distribution channel 180 may have rounded corners, or rounds 188, at the upstream end each intersection with an entrance channel 190. The entrance to each segment of the main distribution channel, 182, 184, and 186, remains sharp cornered, which provides another passive barrier to fluid flow, and encourages fluid to fill the entrance channels 190 prior to advancing into the next segment of the main distribution channel. The rounds 188 and/or surrounding surfaces may thus be either coated with or formed of a hydrophobic material. The passive fluid flow barriers may operate to cause predictable and ordered filling of the wells 158 (i.e., through the first and second flow paths 120, 122 first, then through the third and fourth flow paths 124, 126, and so on) without unduly inhibiting advancement of the fluid through the main distribution channel 180. Another function of rounds 188 is to guide fluid flow into entrance channels 190.

The main distribution channel 180 may generally have a width sufficient to avoid creating a significant flow restriction. From the main distribution channel 180, entrance channels 190 branch to reach the wells 158. The entrance channels 190 may also be large enough to avoid creating a significant flow restriction. The entrance channels 190 may even be somewhat wider than that of the main distribution channel 180. If the entrance channels 190 have larger cross sectional areas than main distribution channel 180, then at each branch point fluid will flow preferentially into the entrance channels 190 to fill the attached wells 158 prior to flowing further downstream in the distribution channel. This will result in the wells being filled sequentially starting with those closest to inlet channel 112. If wells are filled sequentially in this order, it is possible to fill all wells by injecting a quantity of first fluid just sufficient to fill the wells and entrance channels, but not the main distribution channel.

If the entrance channels 190 are smaller than the main distribution channel 180, fluid will flow preferentially through the main distribution channel until it reaches the end opposite inlet channel 112. The wells will not necessarily be filled in any specific sequence if the entrance channels all have substantially the same cross-sectional areas, but if entrance channels vary in cross-sectional area, the wells connected to the larger entrance channels will fill first. In order to ensure that all wells are completely filled, it will be necessary to inject a quantity of first fluid that is sufficient to fill the wells 158, entrance channels 190, and all of main distribution channel 180.

The main distribution channel 180 may have a uniform cross sectional area, despite the fact that the quantity of fluid flowing through the main distribution channel 180 decreases from the first segment 182 to the second segment 184 and from the second segment 184 to the third segment 186. The uniform cross sectional area may facilitate manufacturing, ordered filling of the wells 158, and ordered removal of the fluid from the main distribution channel 180, via the entrance channels 190, when a second fluid is introduced into the inlet channel 112 to flush out the first fluid. The second fluid may fill the main distribution channel 180 prior to entry into any of the entrance channels 190.

The first fluid may be a testing sample, available in limited quantities, while the second fluid may be a bulk washing solution or the like. Hence, the first fluid may most effectively be conserved by introducing the second fluid prior to the time that all of the wells 158 have filled with the first fluid. The second fluid may then fill the main distribution channel 180, leaving the first fluid only in the wells 158 and optionally also in the entrance channels 190. This may avoid the injection of air bubbles. As noted above, it is necessary that the entrance channels 190 have larger cross sectional areas than main distribution channel 180 in order for this filling pattern to be achieved.

As shown, the circuit 110 is generally symmetrical between the left and right sides, aside from the inlet channel 112 and the outlet channel 114. However, the circuit 110 is not symmetrical with respect to each individual flow path. Rather, the first, third, fifth, and seventh flow paths 120, 124, 148, 132 all extend from different portions of the main distribution channel 180, and consequently, all have different lengths. Due to the left-to-right symmetry, the first, third, fifth, and seventh, or odd-numbered, draining portions 160, 164, 168, 172 will be described, with the understanding that the second, fourth, sixth, and eighth, or even-numbered, draining portions 162, 166, 170, 174 are symmetrical to, and thus functionally equivalent to, the odd-numbered draining portions 160, 164, 168, 172, respectively.

Each of the draining portions 160, 164, 168, 172 may have an exit channel array 192 coupled to each of the wells 158 to receive fluid. Each of the exit channel arrays 192 may include multiple exit channels. For example, each exit channel array 192 may have a first exit channel 194, a second exit channel 196, and a third exit channel 198. Of course, a larger or smaller number of exit channels may be used. The presence of multiple exit channels 194, 196, 198 may ensure that each of the exit channel arrays 192 is able to receive fluid from multiple regions of the associated well 158, so that stagnant fluid regions or gas bubbles can be avoid, and the washing efficiency can be enhanced.

Such a configuration facilitates filling of each well 158 by allowing air to pass through the exit channels 194, 196, 198. Since the exit channels 194, 196, 198 are of smaller enough diameter to utilize capillary forces to provide passive pressure barriers, air is able to flow relatively freely into the exit channels 194, 196, 198. The use of multiple exit channels 194, 196, 198 also facilitates washing of the first fluid from the well 158 by preventing a portion of the fluid from stagnating within the well 158 while another portion flows alongside the stagnating portion to reach an outlet.

The exit channels 194, 196, 198 may each have a comparatively small cross sectional area compared to the cross sectional area of the wells 158. Hence, the exit channels 194, 196, 198 may each provide a narrowing that acts as a passive fluid flow barrier. However, the exit channels 194, 196, 198 may each have a depth equal to the depth of the wells 158. If desired, the flow paths 120, 122, 124, 126, 128, 130, 132, 134, the inlet channel 112, the outlet channel 114, extensions channels and the wells 156 may all have an equal depth. Exit channels and extension channels may have similar or identical cross sectional areas. Alternatively, multiple depths may be used to form the exit channels 194, 196, 198, the wells 158, the flow paths 120, 122, 124, 126, 128, 130, 132, 134, the inlet channel 112, and the outlet channel 114. Indeed, the various components of the circuit 110 may even be arranged in three dimensions, if desired.

In order to operate as passive fluid flow barriers, the exit channels 194, 196, 198 may each have surfaces formed of a hydrophobic material. If desired, the entire chip 111 may be formed of a hydrophobic material. In the alternative, the surfaces of the exit channels 194, 196, 198 may simply be coated with a hydrophobic material to provide passive fluid flow barriers or pressure barriers. In either case, the exit channels 194, 196, 198 operate to stop the fluid from flowing into the draining portions 160, 164, 168, 172 until the pressure gradient across the exit channels 194, 196, 198 has reached a predetermined threshold. Hence, the fluid may be kept from exiting the wells 158 by keeping the fluid pressure low enough that the threshold pressure gradient is not surpassed.

The exit channels 194, 196, 198 of each exit channel array 192 may converge to convey the fluid to a first extension channel 200, a third extension channel 202, a fifth extension channel 204, or a seventh extension channel 206, each of which is part of the first draining portion 160, the third draining portion 164, the fifth draining portion 168, or the seventh draining portion 172, respectively.

All of the extension channels 200, 202, 204, 206 convey the fluid to a waste collection channel 210. The waste collection channel 210 may have a first segment 212 disposed between the first and third extension channels 200, 202, a second segment 214 disposed between the third and fifth extension channels 202, 204, and a third segment 216 disposed between the fifth and seventh extension channels 204, 206. Furthermore, the waste collection channel 210 may have a junction segment 218 downstream of the third segment 216. The junction segment 218 may convey fluid from all of the extension channels 200, 202, 204, 206 to the outlet channel 114.

As shown, the filling portions 140, 144, 148, 152 each have a different length. More specifically, the first filling portion 140 includes none of the main distribution channel 180, the third filling portion 144 includes the first segment 182, the fifth filling portion 148 includes the first and second segments 182, 184, and the seventh filling portion 152 includes the first, second, and third segments 182, 184, 186, or the entire main distribution channel 180. Consequently, the first filling portion 140 has the lowest pressure drop, while the third, fifth, and seventh filling portions 144, 148, 152 have increasingly large pressure drops.

As a result, in order to equalize the pressure drops of the flow paths 120, 124, 128, 132, the draining portions 160, 164, 168, 172 must have progressively decreasing pressure drops. The first draining portion 160 includes the first, second, third, and junction segments 212, 214, 216, 218 of the waste collection channel 210, while the third draining portion 164 includes the second, third, and junction segments 214, 216, 218, the fifth draining portion 168 includes the third and junction segments 216, 218, and the seventh draining portion 172 includes only the junction segment 218. Hence, the geometry of the waste collection channel 210 ensures that the draining portions 160, 164, 168, 172 will have progressively decreasing pressure drops.

Nevertheless, the waste collection channel 210 may be of relatively large cross sectional area and thus provide a comparatively low pressure drop; hence, the pressure drops of the draining portions 160, 164, 168, 172 may not differ sufficiently to compensate for the pressure drop differentials of the filling portions 140, 144, 148, 152 without additional adjustment. Hence, the extension channels 200, 202, 204, 206 may also provide progressively lower pressure drops, so that the pressure drops of the flow paths 120, 124, 128, 132 can be fully equalized. More specifically, as depicted in FIG. 2, the first extension channel 200 may be the longest, while the third, fifth, and seventh extension channels 202, 204, 206 become progressively shorter. The pressure drop of a channel is generally proportional to the length of the channel. Thus, the first extension channel 200 has the greatest pressure drop, while those of the third, fifth, and seventh extension channels 202, 204, 206 decline progressively. Like waste collection channel 210, outlet channel 114 has a relatively large cross sectional area, and thus has a low resistance to fluid flow.

As a result, the pressure gradients, or pressure drops, of the flow paths 120, 124, 128, 132 are equal to each other, despite the fact that the flow paths 120, 124, 128, 132 have different lengths. Hence, under wetted fluid circuit conditions, fluid will flow equally readily into any of the flow paths 120, 124, 128, 132. An approximately equal quantity, or equal flow rate, of fluid can therefore be expected flow through each of the flow paths 120, 124, 128, 132.

After the fluid sample processing is complete, the second fluid may be further pressurized to induce the first fluid to flow past the passive fluid flow barriers created by the comparatively small exit channels 194, 196, 198. The first fluid may then substantially simultaneously flow into and through each of the draining portions 160, 164, 168, 172, due to the fact all of the flow paths 120, 124, 128, 132 have substantially the same pressure drop. The result is more accurate timing of the reactions within the wells 158 and conservation of the first and/or second fluids.

In general, a method for moving a first fluid through a microfluidic circuit as described above includes the steps of pressurizing the first fluid to induce it to enter inlet channel 112 and main distribution channel 189, and from there enter the wells 158 via there respective entrance channels, further pressurizing the first fluid to overcome the passive fluid fluid barriers and induce it to flow out of the wells into downstream portions of the flow paths, and continue to pressurize the first fluid to urge it to flow through each of the flow paths. The first fluid may be pressurized by injecting it into the fluid circuit under pressure, or by injecting a second fluid (either liquid or gas, as discussed previously) behind the first fluid to drive it into the fluid circuit. It should be noted that as an alternative to further pressurizing the first fluid to overcome passive fluid flow barriers, active valves (mechanical, pneumatic, electrical, etc.) could be opened to permit fluid to flow out of downstream of the wells.

A more rigorous description of the pressure gradient balancing concept will now be presented, with reference to the circuit 110 of FIG. 2. As shown, several letters have been included to identify various portions of the circuit 110 in addition to the reference numerals; these letters will be used to facilitate mathematical analysis of the pressure drops of the various components of the circuit 110. The following description will proceed with reference to the left side of the circuit 110, with the understanding that a parallel analysis applies to the right side.

The inlet channel 112 is designated "A," the first, second, and third segments 182, 184, 186 of the main distribution channel 180 are designated "B1," "B2," and "B3," and the entrance channels 190 are designated "C." The wells 158 are designated "D," the exit channel arrays 192 are designated "E," and the extension channels 200, 202, 204, 206 are designated "F1," "F2," "F3," and "F4." The first, second, and third segments 212, 214, 216 of the waste collection channel 210 are designated "$G_1$," "$G_2$," and "$G_3$," respectively, while the junction segment 218 is designated "H" and the outlet channel 114 is designated "I."

The left side of the circuit 110 has four flow paths that correspond to the first, third, fifth, and seventh flow paths 120, 124, 128, 132. Let Q be the required flow rate through each of the wells 158, and $\Delta p_n$ (n=A, B, . . . , I) be the pressure drop along each flow path section, as designated above. The equal pressure drop requirement leads to the following equation:

$$\Delta p1 = \Delta p3 = \Delta p5 = \Delta p7 \qquad (1)$$

Where $\Delta p1$, $\Delta p3$, $\Delta p5$, and $\Delta p7$ are the pressure drops on flow paths 120, 124, 128, and 132, respectively. The pressure drop on each flow path is the sum of the pressure drops on each of the sections of the flow path, namely:

$$\Delta p1 = \Delta p_A + \Delta p_C + \Delta p_D + \Delta p_E + \Delta p_{F1} + \Delta p_{G1} + \Delta p_{G2} + \Delta p_{G3} + \Delta p_H + \Delta p_I \quad (2)$$

$$\Delta p3 = \Delta p_A + \Delta p_{B1} + \Delta p_C + \Delta p_D + \Delta p_E + \Delta p_{F2} + \Delta p_{G2} + \Delta p_{G3} + \Delta p_H + \Delta p_I \quad (3)$$

$$\Delta p5 = \Delta p_A + \Delta p_{B1} + \Delta p_{B2} + \Delta p_C + \Delta p_D + \Delta p_E + \Delta p_{F3} + \Delta p_{G3} + \Delta p_H + \Delta p_I \quad (4)$$

$$\Delta p7 = \Delta p_A + \Delta p_{B1} + \Delta p_{B2} + \Delta p_{B3} + \Delta p_C + \Delta p_D + \Delta p_E + \Delta p_{F4} + \Delta p_H + \Delta p_I \quad (5)$$

Equations (2) through (5) can be rewritten as:

$$\Delta p1 = \Delta p_{common} + \Delta p_{F1} + \Delta p_{G1} + \Delta p_{G2} + \Delta p_{G3} \quad (2')$$

$$\Delta p3 = \Delta p_{common} + \Delta p_{B1} + \Delta p_{F2} + \Delta p_{G2} + \Delta p_{G3} \quad (3')$$

$$\Delta p5 = \Delta p_{common} + \Delta p_{B1} + \Delta p_{B2} + \Delta p_{F3} + \Delta p_{G3} \quad (4')$$

$$\Delta p7 = \Delta p_{common} + \Delta p_{B1} + \Delta p_{B2} + \Delta p_{B3} + \Delta p_{F4} \quad (5')$$

where $\Delta p_{common} = \Delta p_A + \Delta p_C + \Delta p_D + \Delta p_E + \Delta p_H + \Delta p_I$, the component of the pressure drop common to all flow paths.

The pressure drop along each section of a flow path can be estimated using the following formula assuming fully developed Newtonian laminar flow, or through numerical simulation for more accurate results:

$$\Delta p = 2\mu Q L P_0/(D_h A) \quad (6)$$

where $\mu$ is the fluid viscosity, Q is the flow rate through the channel section, L is the length of the channel section, $D_h$ is the hydraulic diameter of the channel cross-section, and A is the cross-sectional area. Here $P_0$ is the Poiseuille number of channel flow, whose value is dependent on the shape of channel cross-section.

It should be noted that the flow rates are different in different flow path sections, e.g., inlet channel 112 and outlet channel 114 have flow rates eight times that of any individual well 158, while the first segment 182 of the main distribution channel 180, designated "B1," has a flow rate six times that of each of the wells 158, designated "D" (since it delivers fluid to six downstream wells). As another example, the third segment 216 of the waste collection channel 210, designated "G$_3$," has a flow rate three times that of each of the wells 158, since it drains fluid from three such wells. If it is assumed that segments G1, G2 and G3 have equal resistances to flow under equal flow rates, and segments B1, B2, and B3 have equal resistances to flow under equal flow rates, then the pressure drops over these segments will be proportional to the flow rates on these segments. Thus, it will be the case that $\Delta p_{G2} = 2\Delta p_{G1}$, $\Delta p_{G3} = 3\Delta p_{G1}$, $\Delta p_{B1} = 3 p_{B3}$, and $\Delta p_{B2} = 2\Delta p_{B3}$. Then equations 2' through 5' can be rewritten:

$$\Delta p1 = \Delta p_{common} + \Delta p_{F1} + 6\Delta p_{G1} \quad (2'')$$

$$\Delta p3 = \Delta p_{common} + \Delta p_{F2} + 5\Delta p_{G1} + 3\Delta p_{B3} \quad (3'')$$

$$\Delta p5 = \Delta p_{common} + \Delta p_{F3} + 3\Delta p_{G1} + 5\Delta p_{B3} \quad (4'')$$

$$\Delta p7 = \Delta p_{common} + \Delta p_{F4} + 6\Delta p_{B3} \quad (5'')$$

Here we assume all wells 158, D, entrance channels 190, C, and exit channel arrays 192, E are equal size and shape, and thus have equal resistances to flow.

Equations 2", 3", 4", and 5" may all be set equal to each other and solved to obtain relative weights for $\Delta p_{F1}$, $\Delta p_{F2}$, $\Delta p_{F3}$, and $\Delta p_{F4}$. The configuration of one of the extension channels 200, 202, 204, 206, F1, F2, F3, F4 may then be established, and the configurations of the remaining extension channels 200, 202, 204, 206, F1, F2, F3, F4 may then be established based on the necessary relative pressure drop. A simple way of doing this, for example, would be to set the length of the channel that will be the longest at the longest convenient length (which will depend on the desired size of the chip in which the circuit is to be formed), and then select the lengths of the other channels to give the appropriate relative pressure drops. In this example, only the channel length is varied, and all channels have the same cross-sectional dimensions. As will be described subsequently, other parameters, or combinations of parameters, may be adjusted to give the desired pressure drops.

Of course, the method above represents only one example of a design process that accomplishes pressure drop balancing. Those of skill in the art will recognize that other mathematical approaches may be successfully utilized to accomplish pressure gradient balancing within the scope of the present invention.

The arrangement of the flow paths 120, 122, 124, 126, 128, 130, 132, 134 and well structures 156 of FIG. 2 is only one of many possible arrangements. If desired, the well structures 156 may be laid out in any suitable pattern, and flow paths may be designed to connect them to an inlet and outlet. The flow paths may branch symmetrically or asymmetrically from a single branching point, or they may effectively branch from several locations, as with the main distribution channel 180. In either case, the pressure drops of the flow paths may be balanced to provide substantially equal fluid flow rates under wetted circuit conditions.

Figure 3:
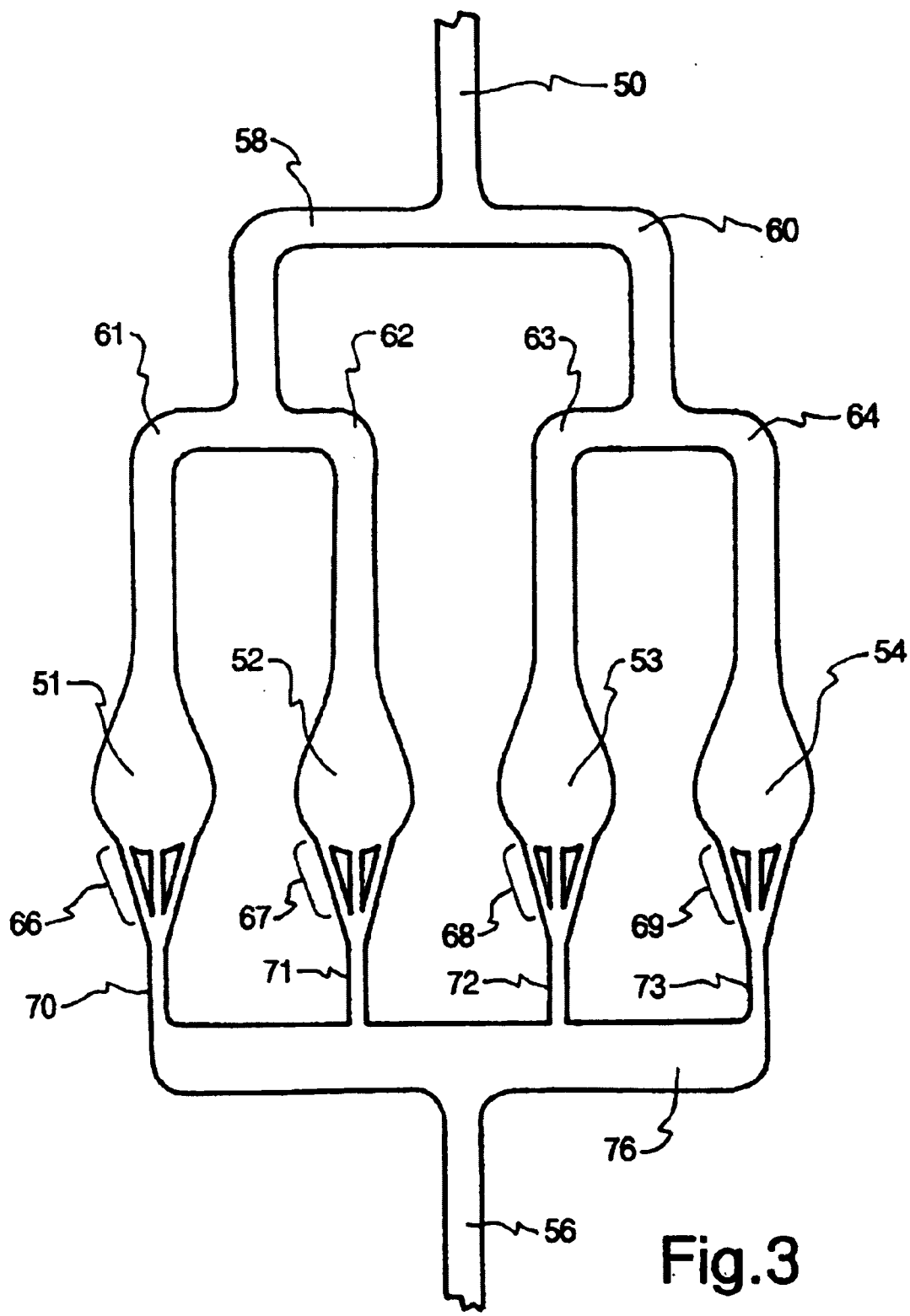
FIG. 3 is a plan view of still another embodiment of a microfluidic circuit within the scope of the invention.

FIG. 3 illustrates another embodiment of the invention in which balanced flow is obtained on multiple flow paths. In this embodiment, fluid enters the microfluidic circuit via inlet channel 50, passes through four parallel flow paths feeding wells 51, 52, 53, and 54 and exits via outlet channel 56. Rather than leading to a single distribution channel that directly feeds a plurality of wells, inlet channel 50 branches to form first generation daughter channels 58 and 60, each of which branches again to form, respectively, second generation daughter channels 61 and 62 and second generation daughter channels 63 and 64. The second generation daughter channels 62, 63, 64 and 64, lead to wells 51, 52, 53, and 54, respectively. Since the first generation daughter channels are equal in length and configuration, and the second generation daughter channels are equal in length and configuration, the filling portions of each of the four flow paths are equal. As described in connection with FIG. 2, each of wells 51, 52, 53 and 54 has an exit channel array 66, 67, 68 or 69, respectively leading out of the well, the channels of the exit channel array merging to form an extension channel 70, 71, 72 or 73. As shown in FIG. 3, exit channel arrays 66–69 and extension channels 70–73 have equivalent configurations, but because the extension channels join waste collection channel 76 at different distances from outlet channel 56, the draining portions of the four flow paths are not completely equivalent. In this case, rather than compensating for the differences in the flow paths by modifying other portions of the flow paths, the problem is overcome by increasing the cross-sectional area of waste collection channel 76 until the difference in resistance to flow on the different flow paths is a negligible percentage of the total resistance to flow. If the depth of a channel is kept constant, and only the width is modified, doubling the channel width leads to the flow resistance being decreased to one fourth of its previous value. It will be appreciated that when waste collection channel 76 is significantly larger diameter than extension channels 70–73, as depicted in FIG. 3, the contribution of waste collection channel 76 to the resistance of each fluid path is negligible.

In addition to channel configurations designed to give equal flow rates on different flow paths, the fluid circuit of FIG. 2 includes other features that improve fluid flow in the circuit. For example, each well 158 in FIG. 2 has a novel configuration that reduces trapping of air bubbles in the well and enhances washing of liquid from the well. These improvements are achieved by using a novel well shape coupled with the use of an array of multiple exit channels at the outlet end of the well. The well is shaped such that the cross sectional area of the well increases gradually from the inlet end to the central region of the well, and then decreases abruptly toward the outlet end of the well, to give the well a generally pear-shaped configuration. The gradual increase in cross-sectional area eliminates the problem of "flow separation" (that is, separation of fluid flowing through the well from the well wall) that leads to vortex regions and dead water by the wall of the well. The exit channel array takes fluid from a broader region of the well than would a single exit channel, which also enhances removal of fluid from the well, as discussed previously.

The well structures 156 of FIG. 2 may be modified in a number of ways to enhance the washing and/or gas removal properties of the circuit 110. Some exemplary alternative well structures will be shown and described in connection with FIGS. 4 and 5. The extension channels 200, 202, 204, 206 may also be configured in a variety of different ways to obtain the desired pressure drop variation. Some exemplary alternatives will be shown and described in connection with FIGS. 6 and 7.

Figure 4:
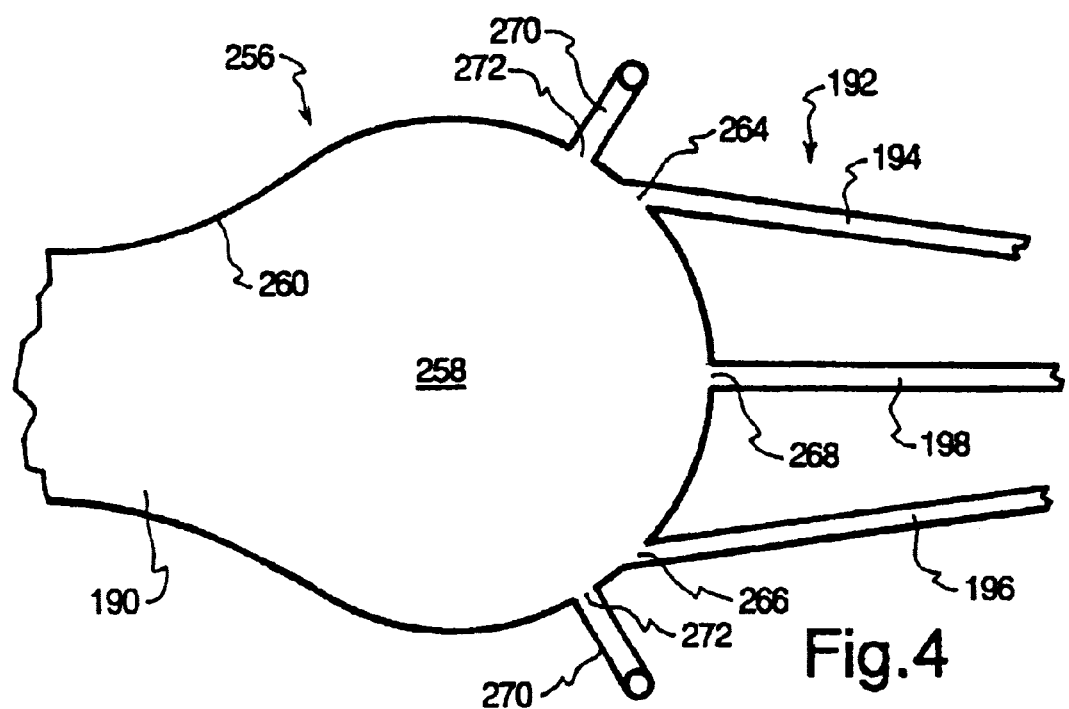
FIG. 4 is a plan view of one alternative embodiment of a well structure for a microfluidic circuit.

Referring to FIG. 4, an alternative embodiment of a well structure 256 suitable for a microfluidic circuit, like the circuit 110, is depicted. Like the well structure 156, the well structure 256 has a well 258 with a rounded shape defined by a wall 260. First, second, and third exit channels 194, 196, 198, like those described previously, may intersect the well 258 at a first juncture 264, a second juncture 266, and a third juncture 268, respectively. The exit channels 194 196, 198 may once again serve as passive fluid flow barriers that receive fluid only when a predetermined pressure gradient has been exceeded.

The well structure 256 may also have one or more vents 270 designed to allow the escape of gas, or more specifically air, from the well 258. The vents 270 may take the form of narrow channels that intersect the well 258 via junctures 272, and that extend to a collection cavity, or simply to the exterior of the chip. The vents 270 may be distributed around the wall 260 of the well 258 to ensure that no significant quantities of air are remain trapped in any portion of the wells 258. Vents 270 may even be disposed between the exit channels 194, 196, 198. In FIG. 4, two vents 270 are depicted. However, more or fewer vents 270 may be utilized.

If desired, each of the vents 270 may have a smaller cross sectional size than the exit channels to provide a passive fluid flow barrier with a somewhat higher pressure threshold than that of the junctures 264, 266, 268 of the exit channels 194, 196, 198. Hence, liquid may be pressurized to flow into the exit channels 194, 196, 198 without attaining the pressure required to enter the vents 270. Each of the vents 270 may alternatively or additionally have a depth much smaller than the depth of the exit channels 194, 196, 198 to help provide the smaller cross sectional area of each vent 270.

Figure 5:
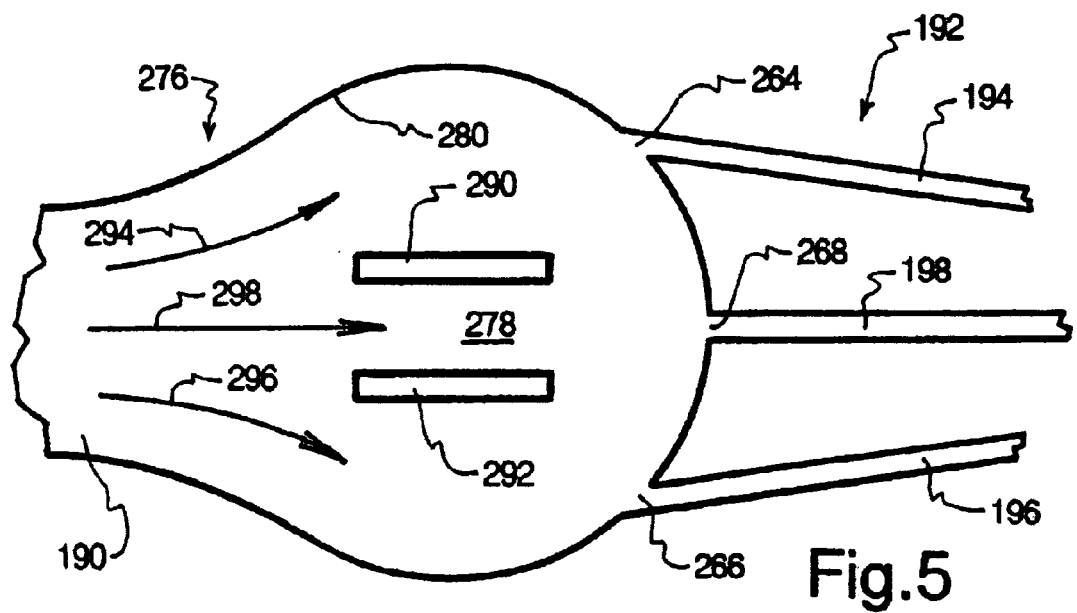
FIG. 5 is a plan view of another alternative embodiment of a well structure for a microfluidic circuit.

Referring to FIG. 5, yet another embodiment of a well structure 276 is depicted, in which flow dividing structures are used to further improve the flow pattern of fluid in the well. The well structure 276 may also be used with a microfluidic circuit, like the circuit 110 of FIG. 2. As with the previous embodiment, the well structure 276 may have a well 278 with a rounded shape defined by a wall 280. First, second, and third exit channels 194, 196, 198, like those of the previous embodiment, may intersect the well 278 at first, second, and third junctures 264, 266, 268, respectively.

A first flow divider 290 may be disposed within the well 278, and may extend from a point near the entrance channel 190 toward the wall 280, between the first and third junctures 264, 268. Similarly, a second flow divider 292 may be disposed within the well 278, and may extend from a point near the entrance channel 190 toward the wall 280, between the second and third junctures 266, 268. Flow dividers may take the form of fins that are attached to one surface of the well and extend partly into the interior of the well, or may extend across the entire height of the well.

The flow dividers 290 may operate to divide the fluid entering the well 278 into a first stream 294, a second stream 296, and a third stream 298. The first stream 294 flows between the first flow divider 290 and the wall 280, the second stream 296 flows between the second flow divider 292 and the wall 280, and the third stream 298 flows between the flow dividers 290, 292. The first, second, and third streams 294, 296, 298 may generally be directed to flow into the first, second, and third exit channels 194, 196, 198, respectively. A single flow divider or more than two flow dividers may also be used within the scope of the invention.

The division of the incoming fluid into multiple streams may facilitate air removal and efficient washing of the well 258. More particularly, the streams 294, 296, 298 may provide a relatively uniform advancement of fluid through the well 258, from the entrance channel 190 to the exit channels 194, 196, 198. Hence, stagnating portions of fluid are further prevented. Although no vents are shown, those of skill in the art will recognize that the use of the flow dividers 290, 292 may be combined with the use of the vents 270 to further enhance air removal. Additionally, the exit channels 194, 196, 198 need not be configured as shown; indeed, more or less exit channels may be used, and a single exit channel may even be used, if desired.

Figure 6:
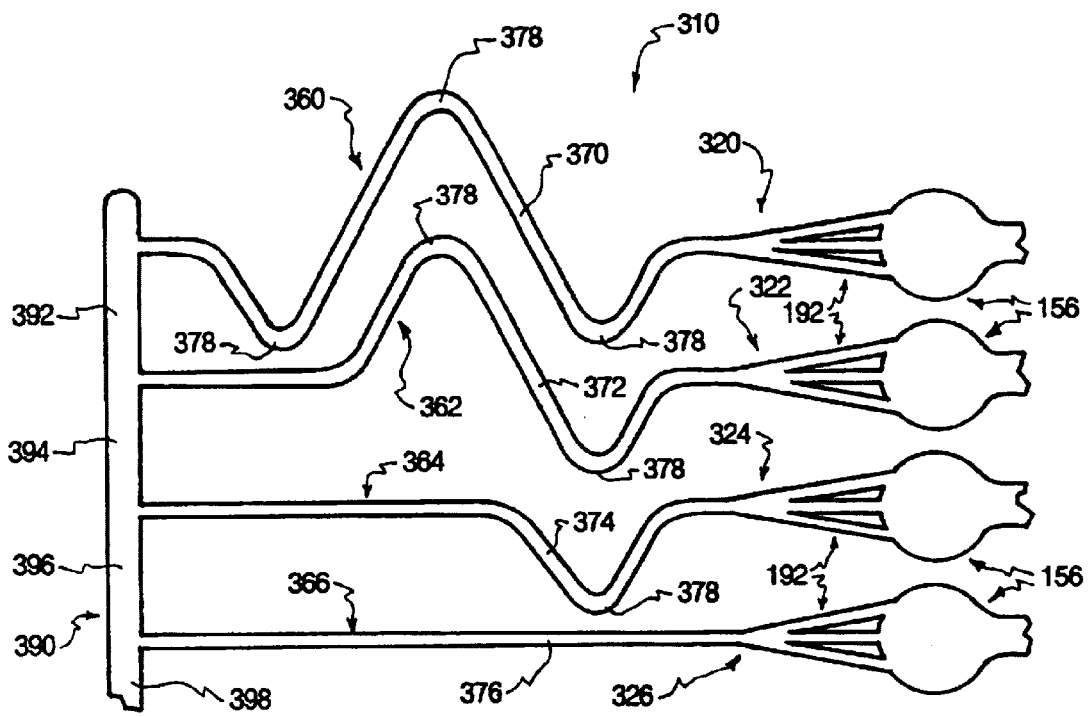
FIG. 6 is a plan view of a portion of another alternative embodiment of a microfluidic circuit within the scope of the invention.

Referring to FIG. 6, a portion of an alternative embodiment of a microfluidic circuit 310, or circuit 310, is depicted. The circuit 310 may be formed in a chip, and may have an inlet channel 112 and an outlet channel 114, like those of FIG. 2. Additionally the circuit 310 may be generally left-to-right symmetrical, or may have only one set of flow paths with no symmetrical set; hence, only one set of flow paths is depicted. This is comparable to the left side of FIG. 2, with fluid flow moving from right to left in the figure. A plurality of well structures 156 is shown, with exit channel arrays 192 like those of the circuit 110 of FIG. 2. The circuit 310 also has first, second, third, and fourth flow paths 320, 322, 324, 326, of which only first, second, third, and fourth draining portions 360, 362, 364, 366 are shown. As in FIG. 2, the draining portions 360, 362, 364, 366 may communicate with and receive fluid from the exit channel arrays 192.

The first, second, third, and fourth draining portions 360, 362, 364, 366 may have first, second, third, and fourth extension channels 370, 372, 374, 376, respectively. As with the circuit 110 of FIG. 2, the filling portions (not shown) may have different pressure drops, and the extension channels 370, 372, 374, 376 may be adjusted to compensate so that each of the flow paths 320, 322, 324, 326 has approximately the same pressure drop.

As with the embodiment of FIG. 2, the extension channels 370, 372, 374, 376 may have progressively decreasing lengths to provide progressively decreasing pressure drops. However, at least some of the extension channels 370, 372, 374, 376 of the circuit 310 may be serpentine in configuration so that all of the extension channels 370, 372, 374, 376 are able to terminate at the same distance from their associated well structures 156.

More particularly, the first extension channel 370 may have three bends 378, so that the first extension channel 370 has the greatest length. The bends 378 may be somewhat dramatic, as shown, or may be gentle, depending on the necessary pressure drop differential. The second extension channel 372 may have two bends 378 to provide a slightly smaller length. The third extension channel 374 may have only a single bend 378 to provide a length smaller than that of the second extension channel 372. The fourth extension channel 376 may be straight to provide the smallest length, and hence, the lowest pressure drop.

The circuit 310 may also have a waste collection channel 390 in communication with each of the extension channels 370, 372, 374, 376. The waste collection channel 390 may have a configuration somewhat similar to that of the waste collection channel 210. Hence, the waste collection channel 390 may have a first segment 392 between the first and second extension channels 372, 374, a second segment 394 between the second and third extension channels 374, 376, a third segment 396 between the third and fourth extension channels 374, 376, and a junction segment 398 that conveys the fluid to the outlet.

However, the waste collection channel 390 need not be angled like the waste collection channel 210. Rather, since the extension channels 370, 372, 374, 376 all terminate at the same distance from their respective well structures 156, the waste collection channel 390 may be disposed parallel to the distribution of the well structures 156. This orientation may serve to make the circuit 310 somewhat more compact, with essentially no loss in function.

Of course, the extension channels 370, 372, 374 need not be serpentine, but may have spiraling, laterally zigzagging, or other shapes that add to the length of the extension channels 370, 372, 374 in a comparatively compact manner. Three dimensional pathways may also be used for the extension channels 370, 372, 374. The fourth extension channel 376 need not necessarily be straight.

Figure 7:
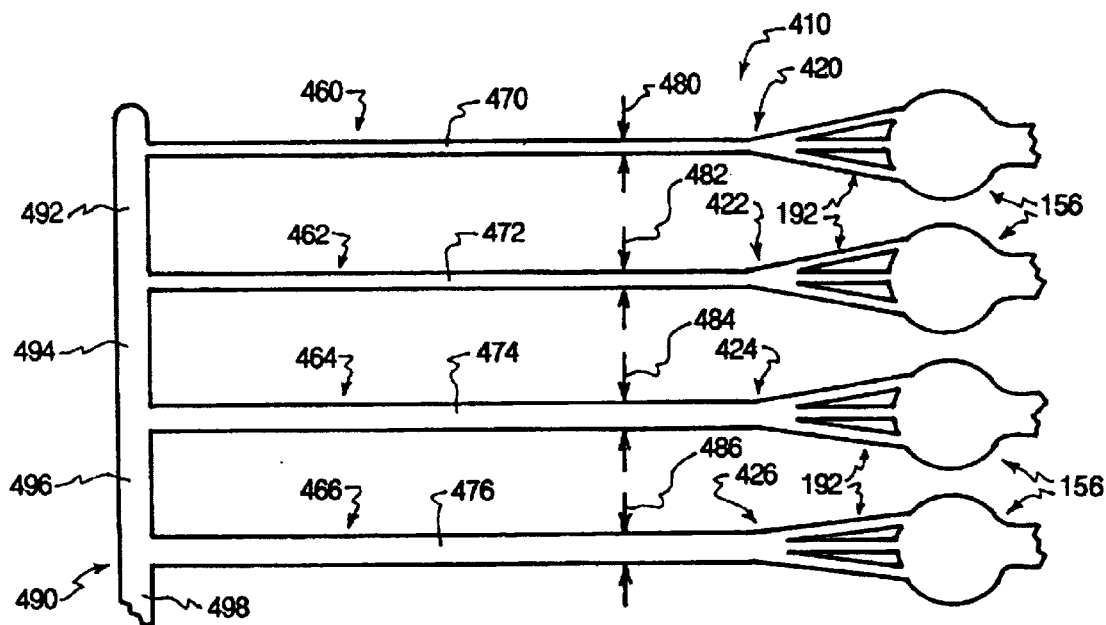
FIG. 7 is a plan view of a portion of another alternative embodiment of a microfluidic circuit within the scope of the invention.

Referring to FIG. 7, a plan view illustrates a portion of a microfluidic circuit 410, or circuit 410, according to another alternative embodiment. As with the previous embodiment, the microfluidic circuit 410 may include addition features not shown, such as an inlet, an outlet, and optionally, a plurality of features symmetrical to those depicted in FIG. 7. FIG. 7 shows a plurality of well structures 156 in communication with first, second, third, and fourth flow paths 420, 422, 424, 426. The first, second, third, and fourth flow paths 420, 422, 424, 426 have first, second, third, and fourth draining portions 460, 462, 464, 466, respectively, that receive fluid from the well structures 156 via exit channel arrays 192.

As with the embodiments of FIGS. 2 and 6, the first, second, third, and fourth draining portions 460, 462, 464, 466 may have first, second, third, and fourth extension channels 470, 472, 474, 476 that receive fluid from the exit channel arrays 192. The extension channels 470, 472, 474, 476 may have different pressure drops to account for pressure drop differentials elsewhere within the flow paths 420, 422, 424, 426.

However, rather than having different lengths, the extension channels 470, 472, 474, 476 may have different cross sectional areas. The extension channels 470, 472, 474, 476 may each have a generally rectangular cross sectional shape. Hence, the cross sectional area may be readily altered by changing the width, the depth, or both the width and depth of each of the extension channels 470, 472, 474, and 476. Since it may be easiest to manufacture the extension channels 470, 472, 474, 476 with a uniform depth, the widths of the extension channels 470, 472, 474, 476 may be modified to provide the necessary pressure drop differentials.

The first extension channel 470 may have a width 480, which is comparatively small. The pressure drop of a channel is generally inversely proportional to the width of the channel if the depth and length are held constant. The first extension channel 470 may thus have a comparatively large pressure drop. The second extension channel 472 may have a width 482 somewhat greater than the width 480. Similarly, the third extension channel 474 may have a width 484 larger than the width 482. The fourth extension channel 476 may have the largest width 486, and therefore, the smallest pressure drop.

As with the previous embodiment, the extension channels 470, 472, 474, 476 may end at substantially the same distances from their respective well structures 156. Thus, waste collection channel 490 may be disposed generally parallel to the distribution of the well structures 156. As with previous embodiments, the waste collection channel 490 may have a first segment 492 between the first and second extension channels 470, 472, a second segment 494 between the second and third extension channels 472, 474, a third segment 496 between the third and fourth extension channels 474, 476, and a juncture segment 498 downstream of the fourth extension channel 476. As with the previous embodiment, the parallel orientation of the waste collection channel 490 enables the circuit 410 to be comparatively compactly arranged.

In the examples herein, extension channels have been depicted as connecting to a waste collection channel that leads to an outlet channel. Alternatively, extension channels may empty into one or more waste reservoirs, or simply lead directly to an outlet channel that leads to some off-device waste collection structure. These and other outlet features may serve to collect fluid from the extension channels and either retain it on the chip or allow it to exit the chip.

Figure 8:
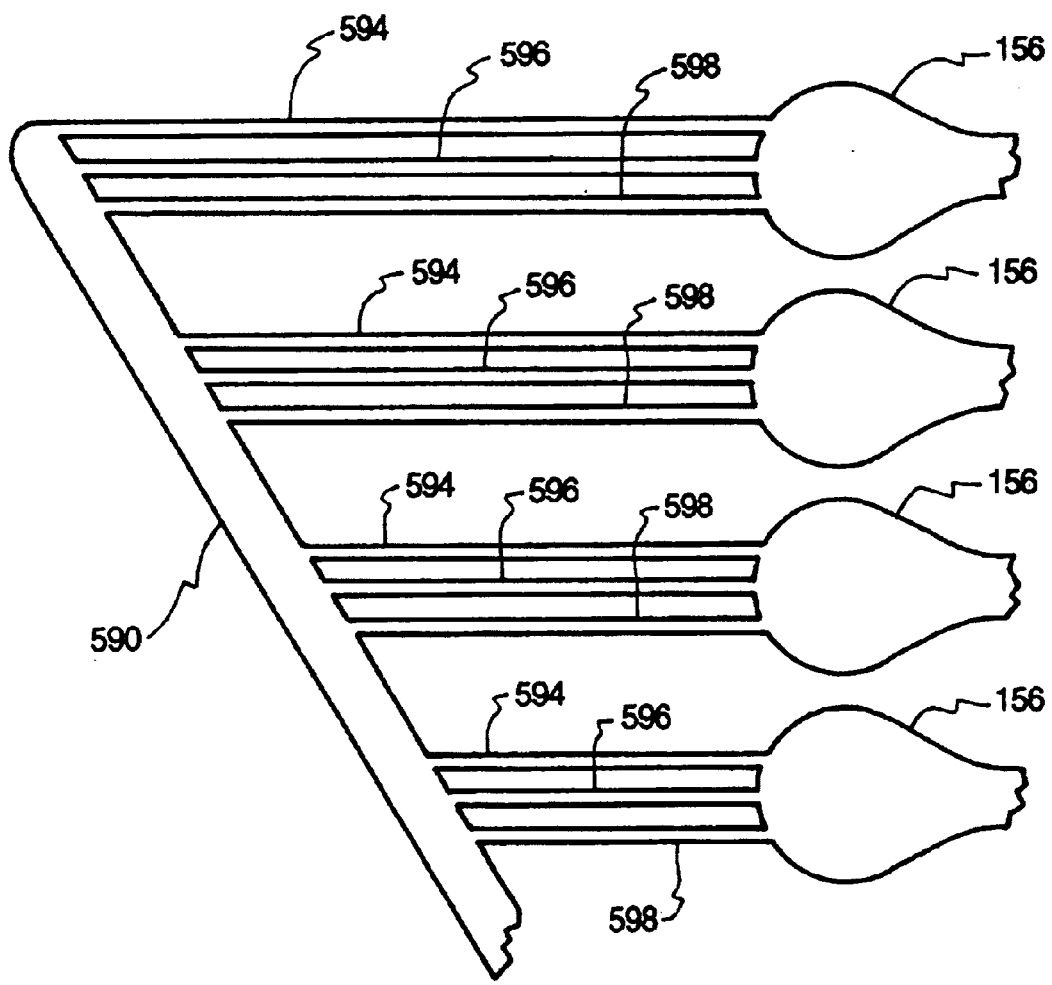
FIG. 8 is a plan view of a portion of yet another alternative embodiment of a microfluidic circuit within the scope of the invention.

As depicted in FIG. 8, another modification to circuits constructed according to the invention is that the extension channels connecting the exit channels to the waste collection channels can be removed, and the exit channels can be extended so that they connect directly to the waste collection channel. Extended exit channels, which connect wells 156 to waste collection channel 590, are indicated by reference numbers 594, 596, and 598 in FIG. 8.

Other methods of providing differential pressure drops, such as variations in cross sectional shape or surface roughness, may be used, but are not illustrated. Of course, the well structures 256, 276 of FIGS. 3 and 4 may be substituted for the well structures 156 in any of the circuits 110, 310, 410 of FIGS. 2, 5, and 6. Additionally, numerous other modifications may be made, as known to those of skill in the art.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A method for moving a first fluid through a microfluidic circuit comprising an inlet, an outlet, a plurality of flow paths providing fluid communication between said inlet and said outlet, and a plurality of wells, wherein each flow path passes through and includes one said well, and wherein the resistances of the flow paths to fluid flow are selected to produce flow rates of fluid through the flow paths in substantially fixed ratios with respect to flow rates through other flow paths under wetted fluid circuit conditions, the method comprising:

pressurizing the first fluid to induce entry of the first fluid through said inlet, into the flow paths, and into said wells to fill said wells;

further pressurizing the first fluid to induce the first fluid to substantially simultaneously commence flowing out of said wells into downstream portions of said flow paths; and continuing to pressurize the first fluid to urge the first fluid to flow through each of the flow paths to move said first fluid through downstream portions of said flow paths, wherein said first fluid flows through said flow paths at relative flow rates defined by the resistances of the flow paths.

2. The method according to claim 1, wherein urging the first fluid to flow through each of the flow paths comprises moving the first fluid through a substantially equal pressure drop in each flow path.

3. The method according to claim 1, wherein moving the first fluid through a substantially equal pressure drop in each flow path comprises moving the first fluid through a plurality of segments in each flow path, wherein corresponding segments of the flow paths are different in length, cross sectional area, or surface roughness.

4. The method according to claim 1, wherein pressurizing the first fluid to induce entry of the first fluid into each of the wells comprises pressurizing the first fluid within the inlet from which the flow paths branch.

5. The method according to claim 1, wherein further pressurizing the first fluid to induce the first fluid to substantially simultaneously commence flowing into downstream portions of the flow paths comprises increasing the fluid pressure to induce the first fluid to flow past a plurality of passive fluid flow barriers positioned within the flow paths.

6. The method according to claim 1, wherein the first fluid is pressurized by pressurizing a second fluid located upstream of and in communication with said first fluid in said microfluidic circuit to urge said first fluid through said microfluidic circuit downstream of said second fluid.

7. The method according to claim 6, wherein the first fluid and second fluid are two different liquids.

8. The method according to claim 6, wherein the first fluid is a liquid and the second fluid is a gas or gaseous mixture.

9. The method according to claim 6, wherein the first fluid and the second fluid are introduced to the inlet via separate ports or channels communicating with said inlet.

10. The method according to claim 6, wherein each flow path comprises an entrance channel leading to the inlet of the well, and wherein a quantity of first fluid moving into the microfluidic circuit followed by the second fluid is just sufficient to fill the wells and entrance channels.

11. The method according to claim 1, wherein the flows through said plurality of flow paths are substantially equal.

12. A microfluidic fluid circuit comprising:
an inlet;
an outlet; and
a plurality of flow paths that branch from the inlet, each providing a fluid connection between the inlet and the outlet; wherein at least a portion of each said flow path comprises a microchannel, and wherein each flow path is configured to produce a predetermined pressure drop for fluid flowing through the flow path at a predetermined flow rate, and wherein the resistance of each said flow path to fluid flow has been selected to produce flow rates of fluid through the flow paths in predetermined ratio with respect to other flow paths under wetted fluid circuit conditions.

13. The microfluidic fluid circuit according to claim 12, wherein at least two of the flow paths contain passive fluid flow barriers, whereby fluid is prevented from advancing past a passive fluid flow barrier under non-wetted fluid circuit conditions until the fluid at the passive fluid flow barrier reaches a threshold pressure, thereby providing controlled filling of a portion of the microfluidic circuit upstream of the passive fluid flow barrier.

14. The microfluidic fluid circuit according to claim 13, wherein each of the passive fluid flow barriers comprises a short microchannel narrowing.

15. The microfluidic fluid circuit according to claim 13, wherein the passive fluid flow barrier is produced by a region of the flow path differs from adjacent regions by having a different cross sectional area, contact angle of the material forming the flow, or surface tension of the flowing fluid.

16. The microfluidic fluid circuit according to claim 13, wherein the passive fluid flow barrier is located in a microchannel and is caused by a modified microchannel surface property, by an abrupt microchannel narrowing, or an abrupt microchannel widening.

17. The microfluidic fluid circuit according to claim 12, wherein the flow paths are configured such that the flow rate on a given flow path is determined with respect to other flow paths by a difference in the length of at least a portion of the flow path.

18. The microfluidic fluid circuit according to claim 12, wherein the flow paths are configured such that the flow rate on a given flow path is determined with respect to other flow paths by a difference in the cross sectional area of at least a portion of the flow path.

19. The microfluidic fluid circuit according to claim 12, wherein the flow paths are configured such that the flow rate on a given flow path is determined with respect to other flow paths by a difference in the surface roughness of at least a portion of the flow path.

20. The microfluidic circuit according to claim 12, wherein the plurality of flow paths comprises at least four flow paths.

21. The microfluidic circuit according to claim 12, wherein each flow path comprises a filling portion and a draining portion, the microfluidic circuit further comprising a plurality of wells, each of which communicates with a flow path to receive fluid from the associated filling portion and to expel fluid to the associated draining portion.

22. The microfluidic circuit according to claim 21, wherein each of the draining portions comprises at least a first exit channel that intersects the associated well via a first juncture to receive fluid from the well, wherein the first exit channel forms a narrowing with respect to the well to provide the passive fluid flow barrier.

23. The microfluidic circuit according to claim 22, wherein the first juncture is either formed of or coated with a hydrophobic material.

24. The microfluidic circuit according to claim 21, further comprising:
a main distribution channel from which entrance channels branch to each of the wells;
a plurality of exit channels;
a plurality of extension channels; and
at least one waste collection channel;
wherein at least one exit channel conveys fluid from each well to an extension channel; each extension channel conveys fluid to the waste collection channel; the filling portion of each flow path comprises an entrance channel and a portion of said main distribution channel between said inlet and said entrance channels; and the draining portion of each flow path comprises at least one exit channel, an extension channel, and at least a portion of said waste collection channel.

25. The microfluidic circuit of claim 24, wherein at least two of the extension channels comprise different length, cross sectional area, shape, or surface roughness characteristics.

26. The microfluidic circuit according to claim 21, further comprising:
a main distribution channel from which entrance channels branch to each of the wells;
a plurality of exit channels; and
at least one waste collection channel;
wherein at least one exit channel conveys fluid from each well to the waste collection channel; the filling portion of each flow path comprises an entrance channel and a portion of said main distribution channel between said inlet and said entrance channels; and the draining portion of each flow path comprises at least one exit channel, an extension channel, and at least a portion of said waste collection channel.

27. The microfluidic circuit of claim 26, wherein at least two of the exit channels comprise different length, cross sectional area, shape, or surface roughness characteristics.

28. The microfluidic circuit according to claim 12, wherein the configurations of the flow paths are designed to produce flow rates that are substantially equal under wetted fluid circuit conditions.

29. The microfluidic circuit according to claim 12, further comprising an outlet into which the flow paths converge.

30. The microfluidic circuit according to claim 12, wherein at least two of the flow paths contain valves to provide controlled filling of a portion of the microfluidic circuit upstream of the valves, said valves selected from the group consisting of mechanically activated valves, thermally activated valves, electrically activated valves, pneumatically activated valves, and hydraulically activated valves.

31. A microfluidic circuit comprising:
an inlet;
an outlet; and
a flow path between said inlet and said outlet, said flow path comprising a well structure in fluid communication between said inlet and said outlet, said well structure comprising:
a well defined by a wall;
a first exit channel that intersects the well via a first juncture with the wall; and
a second exit channel that intersects the well via a second juncture with the wall;
wherein the first and second junctures are displaced from each other along the wall to receive fluid from different portions of the well, each of the first and second junctures comprising an abrupt narrowing that forms a passive fluid flow barrier tending to restrict advancement of fluid from the well into the exit channel.

32. The microfluidic circuit according to claim 31, wherein said well structure further comprises a third exit channel that intersects the well via a third juncture with the wall, wherein the third juncture is displaced from the first and second junctures along the wall, wherein the third juncture comprises an abrupt narrowing that forms a passive fluid flow barrier.

33. The microfluidic circuit according to claim 32, wherein said well structure further comprises an entrance channel that conveys fluid into the well, wherein the entrance channel is disposed directly opposite the second juncture.

34. The microfluidic circuit according to claim 33, wherein the first and third junctures are symmetrically disposed on either side of the second juncture so that fluid proximate the wall between the first juncture and the entrance channel is generally directed into the first juncture, and fluid proximate the wall between the third juncture and the entrance channel is generally directed into the third juncture.

35. The microfluidic circuit according to claim 31, wherein the first and second exit channels join each other downstream from the well.

36. The microfluidic circuit according to claim 31, wherein the first and second junctures are positioned to receive gas bubbles from the well to facilitate removal of gas from the well.

37. A microfluidic circuit comprising:
an inlet;
an outlet; and
a flow path between said inlet and said outlet, said flow path comprising a well structure in fluid communication between said inlet and said outlet, said well structure comprising:
a well defined by a wall;
a first exit channel that intersects the well via a first juncture with the wall; and
a first flow divider positioned within the well to separate fluid entering the well into first and second streams, at least one of which is oriented to direct fluid proximate the wall toward the first juncture.

38. The microfluidic circuit according to claim 37, wherein said well structure further comprises a-second exit channel that intersects the well via a second juncture with the wall, wherein the first flow divider is positioned to direct the first flow into the first exit channel and the second flow into the second exit channel.

39. The microfluidic circuit according to claim 38, wherein said well structure further comprises a second flow divider positioned alongside the first flow divider so that fluid entering the well is further separated to form a third flow.

40. The microfluidic circuit according to claim 39, wherein said well structure further comprises a third exit channel that intersects the well via a third juncture with the wall, wherein the third exit channel is positioned to receive the third flow.

41. A microfluidic circuit comprising:
an inlet;
an outlet; and
a flow path between said inlet and said outlet, said flow path comprising a well structure in fluid communication between said inlet and said outlet, said well structure comprising:
  a well defined by a wall and having an inlet end and an outlet end; and
  a first exit channel that intersects the well via a first juncture with the wall at said outlet end;
  wherein the cross sectional area of said well increases gradually from said inlet end to the central region of said well, and decreases abruptly from the central region of said well to said outlet end, to give said well a generally pear-shaped configuration.

42. A microfluidic circuit comprising:
an inlet; and
at least two flow paths that branch from the inlet, each flow path comprising:
  a fluid handling structure;
  a filling portion adapted to receive fluid from the inlet and deliver fluid to the fluid handling structure; and
  a draining portion adapted to receive fluid from the fluid handling structure;
  wherein each flow path has a resistance to fluid flow that has been selected to produce flow rates of fluid through the flow paths in predetermined ratio with respect to other flow paths under wetted fluid circuit conditions.

43. The microfluidic circuit according to claim 42, wherein the fluid handling structure comprises a well.

44. The microfluidic circuit according to claim 42, wherein the fluid handling structure comprises a channel.

45. The microfluidic circuit according to claim 42, wherein the fluid handling structure comprises a chamber containing a matrix material.

46. The microfluidic circuit according to claim 42, wherein the resistances of the flow paths are in a predetermined ratio to give flows in a predetermined ratio when the pressure drops over the flow paths are equal.

47. The microfluidic circuit according to claim 42, wherein the resistances of the, flow paths to fluid flow are in fixed proportion with respect to each other to give uniform flow through the flow paths when the pressure drops over the flow paths are in the same said fixed proportion with respect to each other.

48. The microfluidic circuit according to claim 42, wherein each flow path further comprises a passive fluid flow barrier downstream of said fluid handing structure, wherein said passive fluid flow barriers on said flow paths cause fluid entering said fluid circuit under non-wetted conditions to fill all fluid handling structures before moving into portions of said microfluidic circuit downstream of said passive fluid flow barrier.

49. The microfluidic circuit according to claim 42, wherein the draining portions of said flow paths are unequal to each other in length.

50. The microfluidic circuit according to claim 42, wherein each flow path comprises a passive fluid flow barrier that causes fluid advancing through the microfluidic circuit preferably to flow in an adjoining flow path connected upstream of said passive fluid flow barrier rather than to flow past said passive fluid flow barrier to provide controlled filling of a portion of the microfluidic circuit.

51. A microfluidic circuit comprising:
an inlet,
a main distribution channel adapted to receive fluid from said inlet; and
a plurality of entrance channels branching off said main distribution channel at multiple locations to deliver fluid to a plurality of flow paths, said entrance channels having cross-sectional areas or shapes selected in relation to the cross-sectional area of said main distribution channel such that when said microfluidic circuit is nonwetted fluid flows preferentially into and fills said main distribution channel before flowing into said entrance channels, and wherein the resistance of each said flow path to fluid flow has been selected to produce flow rates of fluid through the flow paths in predetermined ratio with respect to other flow paths under wetted fluid circuit conditions.

52. The microfluidic circuit of claim 51, further comprising
  a plurality of wells, each adapted to receive fluid from said main distribution channel via one said entrance channel and sized to permit a desired fluid handling step to be performed within said well;
  a plurality of extension channels, each having at least one microscale dimension and adapted to receive fluid from one said well; and
  at least one outlet feature adapted to receive fluid from said plurality of extension channels;
  wherein said plurality of flow paths lead from said inlet to said outlet feature and are defined by said fluid circuit, each flow path comprising at least one said entrance channel, one said well, and one said extension channel, and at least a portion of at least one of said main distribution channel and said outlet feature; wherein said microfluidic circuit is configured to provide fluid flows in predetermined ratio to each other on said flow paths by providing predetermined resistances to fluid flow on all flow paths.

53. The microfluidic circuit of claim 51 wherein the resistances of said extension channels to fluid flow are designed to differ from the extension channels on other flow paths to compensate for differences in resistance to fluid flow in other portions of the flow paths.

54. The microfluidic circuit of claim 51, wherein the resistances of said extension channels vary due to differences with respect to other extension channels in at least one of the extension channel length, depth, width, diameter, or surface roughness.

55. The microfluidic circuit of claim 51, wherein said at least one outlet feature comprises an outlet channel.

56. The microfluidic circuit of claim 51, wherein said at least one outlet feature comprises a waste reservoir.

57. The microfluidic circuit of claim 51, wherein said at least one outlet feature comprises a waste collection channel leading to an outlet channel.

58. The microfluidic circuit of claim 51, further comprising a plurality of exit channel arrays, each exit channel array in fluid communication between one said well and one said extension channel.

59. The microfluidic circuit of claim 51, further comprising a passive fluid flow barrier between said well and said extension channel, said passive fluid flow barrier temporarily stopping the flow of fluid entering said microfluidic circuit, fluid flow being stopped after said well has been filled and resuming after fluid entering said microfluidic circuit has attained a predefined pressure level.

* * * * *